United States Patent
Kingsley et al.

(10) Patent No.: US 12,419,705 B2
(45) Date of Patent: Sep. 23, 2025

(54) ARTICULATION ASSEMBLY FOR ROBOTIC DEVICE

(71) Applicant: Covidien LP, Mansfield, MA (US)

(72) Inventors: Dylan R. Kingsley, Broomfield, CO (US); Christopher T. Tschudy, Arvada, CO (US); Jason G. Weihe, Longmont, CO (US); Zachary S. Heiliger, Nederland, CO (US); William R. Whitney, Boulder, CO (US); Curtis M. Siebenaller, Frederick, CO (US); Haralambos P. Apostolopoulos, Westminster, CO (US); Russell W. Holbrook, Naples, FL (US)

(73) Assignee: Covidien LP, Mansfield, MA (US)

( * ) Notice: Subject to any disclaimer, the term of this patent is extended or adjusted under 35 U.S.C. 154(b) by 434 days.

(21) Appl. No.: 18/101,333

(22) Filed: Jan. 25, 2023

(65) Prior Publication Data
US 2023/0270512 A1  Aug. 31, 2023

Related U.S. Application Data

(60) Provisional application No. 63/313,777, filed on Feb. 25, 2022, provisional application No. 63/313,788, (Continued)

(51) Int. Cl.
*A61B 18/14* (2006.01)
*A61B 34/30* (2016.01)
(Continued)

(52) U.S. Cl.
CPC .......... *A61B 34/30* (2016.02); *A61B 18/1445* (2013.01); *B25J 9/104* (2013.01);
(Continued)

(58) Field of Classification Search
CPC ............ A61B 18/1442; A61B 18/1445; A61B 2017/00477; A61B 2018/00166;
(Continued)

(56) References Cited

U.S. PATENT DOCUMENTS

| 5,752,973 A | 5/1998 | Kieturakis |
| 5,792,135 A | 8/1998 | Madhani et al. |

(Continued)

FOREIGN PATENT DOCUMENTS

| EP | 2783653 A1 | 10/2014 |
| WO | 2017136710 A2 | 8/2017 |

OTHER PUBLICATIONS

Extended Search Report EP23158900.3 dated Jul. 11, 2023, 5 pages.

(Continued)

*Primary Examiner* — Michael F Peffley

(57) ABSTRACT

An articulating electrosurgical instrument includes a housing having an elongated shaft extending therefrom and a wrist assembly operably supported to a distal end of the elongated shaft and configured to support an end effector assembly at distal end thereof. The wrist assembly includes a proximal link operably coupled to the distal end of the elongated shaft, a distal link operably coupled to the end effector assembly, and a central link operably coupled between the proximal link and the distal link. A transition lumen is configured to be received within the distal link, central link and proximal link. The transition lumen includes a helical passageway defined therein configured to guide a blade rod therethrough for operable engagement with a blade disposed within the end effector assembly.

17 Claims, 17 Drawing Sheets

Related U.S. Application Data filed on Feb. 25, 2022, provisional application No. 63/313,793, filed on Feb. 25, 2022, provisional application No. 63/313,790, filed on Feb. 25, 2022, provisional application No. 63/313,775, filed on Feb. 25, 2022, provisional application No. 63/313,797, filed on Feb. 25, 2022, provisional application No. 63/313,781, filed on Feb. 25, 2022.

(51) Int. Cl.
*B25J 9/10* (2006.01)
*B25J 17/02* (2006.01)
*A61B 18/00* (2006.01)

(52) U.S. Cl.
CPC ..... *B25J 17/02* (2013.01); *A61B 2018/00589* (2013.01); *A61B 2018/00595* (2013.01); *A61B 2018/0063* (2013.01); *A61B 2018/1455* (2013.01); *A61B 2034/306* (2016.02)

(58) Field of Classification Search
CPC .......... A61B 2018/00184; A61B 2018/00589; A61B 2018/00595; A61B 2018/00607; A61B 2018/0063; A61B 2018/1455; A61B 2034/306; A61B 34/30; A61B 34/35; A61B 34/71; B25J 17/02; B25J 9/104

See application file for complete search history.

(56) References Cited

U.S. PATENT DOCUMENTS

| | | | |
|---|---|---|---|
| 5,848,986 A | | 12/1998 | Lundquist et al. |
| 6,817,974 B2 | | 11/2004 | Cooper et al. |
| 7,799,028 B2 | | 9/2010 | Schechter et al. |
| 7,861,906 B2 | | 1/2011 | Doll et al. |
| 7,918,230 B2 | | 4/2011 | Whitman et al. |
| 8,357,161 B2 * | | 1/2013 | Mueller ............. A61B 18/1445 606/205 |
| 8,475,453 B2 * | | 7/2013 | Marczyk ............. A61B 18/1445 606/51 |
| 8,579,176 B2 | | 11/2013 | Smith et al. |
| 9,055,961 B2 * | | 6/2015 | Manzo ................... A61B 34/30 |
| 9,474,569 B2 | | 10/2016 | Manzo et al. |
| 10,874,465 B2 * | | 12/2020 | Weir ................. A61B 18/1442 |
| 2002/0099371 A1 | | 7/2002 | Schulze et al. |
| 2002/0177842 A1 | | 11/2002 | Weiss |
| 2003/0036748 A1 | | 2/2003 | Cooper et al. |
| 2003/0125734 A1 | | 7/2003 | Mollenauer |
| 2003/0208186 A1 | | 11/2003 | Moreyra |
| 2006/0022015 A1 | | 2/2006 | Shelton et al. |
| 2006/0025811 A1 | | 2/2006 | Shelton |
| 2006/0161138 A1 | | 7/2006 | Orban et al. |
| 2007/0233052 A1 | | 10/2007 | Brock |
| 2008/0015631 A1 | | 1/2008 | Lee et al. |
| 2010/0179540 A1 | | 7/2010 | Marczyk et al. |
| 2010/0274265 A1 | | 10/2010 | Wingardner et al. |
| 2010/0292691 A1 | | 11/2010 | Brogna |
| 2011/0118707 A1 | | 5/2011 | Burbank |
| 2011/0118708 A1 | | 5/2011 | Burbank et al. |
| 2011/0118709 A1 | | 5/2011 | Burbank |
| 2011/0118754 A1 | | 5/2011 | Dachs, II et al. |
| 2011/0290853 A1 | | 12/2011 | Shelton, IV et al. |
| 2014/0276723 A1 | | 9/2014 | Parihar et al. |
| 2017/0042560 A1 | | 2/2017 | Lee et al. |
| 2019/0201137 A1 | | 7/2019 | Shelton, IV et al. |
| 2020/0138508 A1 | | 5/2020 | Davison et al. |
| 2020/0246086 A1 | | 8/2020 | Anglese |
| 2020/0397522 A1 | | 12/2020 | Ratia et al. |
| 2021/0052332 A1 | | 2/2021 | Saulenas et al. |
| 2022/0039895 A1 | | 2/2022 | Adams et al. |
| 2022/0079660 A1 * | | 3/2022 | Kingsley ................ A61B 34/71 |
| 2023/0310807 A1 * | | 10/2023 | Heye ................ A61M 25/0147 604/528 |

OTHER PUBLICATIONS

Extended European Search Report for European Patent Application No. 24210396.8 mailed Jan. 23, 2025, 11 pages.

Extended European Search Report issued in corresponding European Application No. 20154024.2 dated Jun. 26, 2020, 9 pages.

Extended European Search Report issued in corresponding European Application No. 20157439.9 dated Jun. 25, 2020, 9 pages.

* cited by examiner

ARTICULATION ASSEMBLY FOR ROBOTIC DEVICE

CROSS-REFERENCE TO RELATED APPLICATION

This application claims the benefit of and priority to U.S. Provisional Applications Ser. Nos. 63/313,775, 63/313,777, 63/313,790, 63/313,793, 63/313,788, 63/313,797, and 63/313,781, all of which were filed on Feb. 25, 2022, the entire contents of each of these applications being incorporated by reference herein.

FIELD

The present disclosure relates to surgical instruments and, more specifically, to articulation assemblies for surgical instruments, such as for use in robotic surgical systems.

BACKGROUND

Robotic surgical systems are increasingly utilized in various different surgical procedures. Some robotic surgical systems include a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument.

A surgical forceps, one type of instrument capable of being utilized with a robotic surgical system, relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, the jaw members need to be manipulated about the tissue prior to tissue treatment. As such, the shaft is articulated in various directions (rotation, pitch, and yaw) to position the jaw members about tissue for tissue treatment, e.g., sealing, or to position the jaw members for dissection purposes. Once tissue is grasped and treated, the tissue is severed using a cutting element.

SUMMARY

As used herein, the term "distal" refers to the portion that is being described which is further from an operator (whether a human surgeon or a surgical robot), while the term "proximal" refers to the portion that is being described which is closer to the operator. The terms "about," "substantially," and the like, as utilized herein, are meant to account for manufacturing, material, environmental, use, and/or measurement tolerances and variations, and in any event may encompass differences of up to 10%. Further, to the extent consistent, any of the aspects described herein may be used in conjunction with any or all of the other aspects described herein.

Provided in accordance with aspects of the present disclosure is an articulating electrosurgical instrument including a housing having an elongated shaft extending therefrom and a wrist assembly operably supported at a distal end of the elongated shaft and configured to support an end effector assembly at distal end thereof. The wrist assembly includes: a proximal link operably coupled to the distal end of the elongated shaft; a distal link operably coupled to the end effector assembly; and a central link operably coupled between the proximal link and the distal link. A transition lumen is configured to be received within the distal link, central link and proximal link and includes a helical passageway defined therein configured to guide a blade rod therethrough for operable engagement with a blade disposed within the end effector assembly.

In aspects according to the present disclosure, the transition lumen includes a central passageway defined therein configured to guide a cam rod for reciprocation therethrough that actuates the end effector assembly upon translation thereof. In other aspects according to the present disclosure, the transition lumen includes a helical lead passageway defined therein configured to guide one or more electrical leads therethrough and into the end effector assembly. In still other aspects according to the present disclosure, a distal end of the transition lumen includes a cap configured to mechanically engage a corresponding mechanical interface disposed at a distal end of the distal link.

In aspects according to the present disclosure, a proximal end of the transition lumen is keyed to mechanically engage a corresponding mechanical interface disposed within the proximal link.

In aspects according to the present disclosure, the transition lumen includes a cap configured to mechanically engage a corresponding mechanical interface disposed at a distal end of the distal link, a key-like interface disposed at a proximal end thereof configured to mechanically engage a corresponding mechanical interface disposed within the proximal link, and a stem disposed therebetween. In other aspects according to the present disclosure, the transition lumen includes a taper disposed between the cap and the stem configured to facilitate engagement within distal link.

In aspects according to the present disclosure, the cap is configured to receive a transition plug therein, the transition plug operably coupling to the end effector assembly. In other aspects according to the present disclosure, the transition plug includes opposing tangs on an outer surface thereof configured to receive complementary mechanical interfaces defined within the transition lumen to secure the transition plug within the transition lumen. In still other aspects according to the present disclosure, the transition plug includes a passageway defined therein configured to guide the blade rod therethrough for operable engagement with the blade disposed within the end effector assembly. In yet other aspects according to the present disclosure, the transition plug includes a central passageway defined therein configured to guide a drive rod for reciprocation therethrough that actuates the end effector assembly upon translation thereof.

In aspects according to the present disclosure, the transition plug includes a lead passageway defined therein configured to guide one or more electrical leads therethrough and into the end effector assembly. In other aspects according to the present disclosure, the passageway of the transition plug and the helical passageway of the transition lumen are disposed in registration with one another to facilitate guiding the blade rod into the end effector assembly.

In aspects according to the present disclosure, a central passageway defined in the transition plug and a central passageway defined in the transition lumen are disposed in registration with one another to facilitate reciprocation of a cam rod therethrough that actuates the end effector assembly upon translation thereof.

In aspects according to the present disclosure, a cut-out defined in the transition plug and a lead passageway defined in the transition lumen are disposed in registration with one another to facilitate reception of one or more electrical leads therethrough.

In aspects according to the present disclosure, the transition lumen is made from a rubber-like or compliant material configured to bend upon articulation of the wrist assembly. In other aspects according to the present disclosure, the transition lumen is made from a moldable thermoplastic polyurethane.

Provided in accordance with additional aspects of the present disclosure is an articulating electrosurgical instrument including a housing having an elongated shaft extending therefrom and a wrist assembly operably supported to a distal end of the elongated shaft and configured to support an end effector assembly at distal end thereof. An articulation actuator is configured to articulate the end effector relative to the elongated shaft upon actuation thereof and a transition lumen is configured to be received within the wrist assembly. The transition lumen includes a helical passageway defined therein configured to guide a blade rod therethrough for operable engagement with a blade disposed within the end effector assembly.

In aspects according to the present disclosure, the transition lumen is made from a rubber-like or compliant material configured to bend upon articulation of the wrist assembly. In other aspects according to the present disclosure, the transition lumen includes a cap configured to mechanically engage a distal end of the wrist assembly, a key-like interface disposed at a proximal end thereof configured to mechanically engage a corresponding mechanical interface disposed within a proximal end of the wrist assembly, and a stem disposed therebetween. In yet other aspects according to the present disclosure, the transition lumen includes a taper disposed between the cap and the stem configured to facilitate engagement within the wrist assembly. In still other aspects according to the present disclosure, the cap is configured to receive a transition plug therein, the transition plug operably coupling to the end effector assembly.

In aspects according to the present disclosure, the transition lumen includes a central passageway defined therein configured to guide a cam rod for reciprocation therethrough that actuates the end effector assembly upon translation thereof. In other aspects according to the present disclosure, the transition lumen includes a helical lead passageway defined therein configured to guide one or more electrical leads therethrough and into the end effector assembly.

In aspects according to the present disclosure, the transition plug includes opposing tangs on an outer surface thereof configured to receive complementary mechanical interfaces defined within the transition lumen to secure the transition plug within the transition lumen. In other aspects according to the present disclosure, the transition plug includes a transition passageway defined therein configured to guide the blade rod therethrough for operable engagement with the blade disposed within the end effector assembly. In aspects according to the present disclosure, the transition passageway of the transition plug and the helical passageway of the transition lumen are disposed in registration with one another to facilitate guiding the blade rod into the end effector assembly.

In aspects according to the present disclosure, the transition plug includes a central passageway defined therein configured to guide a cam rod for reciprocation therethrough that actuates the end effector assembly upon translation thereof. In yet other aspects according to the present disclosure, the transition plug includes a lead passageway defined therein configured to guide one or more electrical leads therethrough and into the end effector assembly.

In aspects according to the present disclosure, a central passageway defined in the transition plug and a central passageway defined in the transition lumen are disposed in registration with one another to facilitate reciprocation of a cam rod therethrough that actuates the end effector assembly upon translation thereof.

In aspects according to the present disclosure, a cut-out defined in the transition plug and a lead passageway defined in the transition lumen are disposed in registration with one another to facilitate reception of one or more electrical leads therethrough.

In aspects according to the present disclosure, the transition lumen is made from a rubber-like or compliant material configured to bend upon articulation of the wrist assembly.

In aspects according to the present disclosure, the transition lumen is made from a moldable thermoplastic polyurethane.

Provided in accordance with additional aspects of the present disclosure is an articulating electrosurgical instrument including a housing having an elongated shaft extending therefrom and a wrist assembly operably supported to a distal end of the elongated shaft and configured to support an end effector assembly at distal end thereof. An articulation actuator is configured to articulate the end effector relative to the elongated shaft upon actuation thereof. A blade actuator is configured to transition a blade rod through the elongated shaft to actuate a blade disposed within the end effector assembly. The transition plug operably couples between the distal end of the elongated shaft and a proximal end of the end effector assembly, the transition plug including a transition passageway defined therein configured to guide the blade rod therethrough for operable engagement with the blade disposed within the end effector assembly.

In aspects according to the present disclosure, the transition plug includes a central passageway defined therethrough configured to guide a cam rod operably coupled to the end effector assembly and configured to actuate the end effector assembly upon translation thereof. In other aspects according to the present disclosure, the transition plug includes a lead passageway defined therein configured to guide one or more electrical leads therethrough and into the end effector assembly.

In aspects according to the present disclosure, the wrist assembly includes a transition lumen extending therethrough and wherein the passageway of the transition plug is disposed in registration with a helical transition passageway defined in the transition lumen to facilitate guiding the blade rod into the end effector assembly.

In aspects according to the present disclosure, the transition plug includes at least one relief channel defined in a face thereof configured to mechanically couple with the end effector assembly.

In aspects according to the present disclosure, the end effector assembly includes opposing jaw members movable relative to one another upon reciprocation of the cam rod and wherein proximal flanges of the opposing jaw members are configured to mechanically seat within corresponding relief channels defined in a face of the transition plug.

In aspects according to the present disclosure, the wrist assembly includes a transition lumen extending therethrough, a distal end of the transition lumen configured to mechanically receive the transition plug. In other aspects according to the present disclosure, the transition lumen includes a cap configured to mechanically engage a distal end of the wrist assembly, the cap configured to receive the transition plug therein. In yet other aspects according to the present disclosure, the transition plug includes opposing tangs on an outer surface thereof configured to receive complementary mechanical interfaces defined within the transition lumen to secure the transition plug within the transition lumen.

Provided in accordance with additional aspects of the present disclosure is an articulating electrosurgical instrument including a housing having an elongated shaft extending therefrom and a wrist assembly operably supported to a distal end of the elongated shaft and configured to support an end effector assembly at distal end thereof. The wrist assembly includes a proximal link operably coupled to the distal end of the elongated shaft, a distal link operably coupled to the end effector assembly, and a central link operably coupled between the proximal link and the distal link. An articulation actuator is disposed within the housing and configured to articulate the wrist assembly upon actuation thereof. The articulation actuator includes a plurality of actuation cables operably associated therewith coupled in opposing pairs such that proximal movement of one of the actuation cables of an opposing pair of actuation cables causes distal movement of the other actuation cable of the pair of actuation cables, each pair of actuation cables including a crimp at a distal end thereof, each crimp of each pair of actuation cables configured to seat within a corresponding pocket defined in the distal link.

In aspects according to the present disclosure, the wrist assembly includes a transition lumen configured to be received within at least the distal link, central link and proximal link, the pairs of articulation cables configured extend along an outer peripheral surface of the transition lumen through the wrist assembly. In other aspects according to the present disclosure, the transition lumen is configured to retain each crimp within each corresponding pocket. In yet other aspects according to the present disclosure, the transition lumen includes a cap configured to mechanically engage a distal end of the wrist assembly, a portion of the cap configured to retain each crimp within each corresponding pocket.

In aspects according to the present disclosure, the proximal link includes railways defined therein configured to guide the articulation cables through the wrist assembly.

Provided in accordance with additional aspects of the present disclosure is an articulating electrosurgical instrument including a housing having an elongated shaft extending therefrom and a wrist assembly operably supported to a distal end of the elongated shaft and configured to support an end effector assembly at distal end thereof. The wrist assembly includes a proximal link disposed proximate to the distal end of the elongated shaft, a distal link operably coupled to the end effector assembly, and a central link operably coupled between the proximal link and the distal link. A back transition plug is operably coupled to the proximal link and operably coupled to the elongated shaft at a distal end thereof, the back transition plug including a series of passageways defined therein configured to pass one or more actuation elements therethrough.

In aspects according to the present disclosure, the housing includes an actuation assembly disposed therein configured to translate a cam rod upon actuation thereof, the cam rod, in turn, actuating the end effector assembly and wherein the back transition plug includes a central passageway defined therethrough for reciprocating the cam rod. In other aspects according to the present disclosure, the housing includes a blade actuator disposed therein configured to translate a blade rod upon actuation thereof and wherein the back transition plug includes a second passageway defined therethrough for reciprocating the blade rod. In yet other aspects according to the present disclosure, the housing includes a series of leads extending therethrough for supplying energy to the end effector assembly and wherein the back transition plug includes a third passageway defined therein for guiding the leads therethrough to the end effector assembly.

In aspects according to the present disclosure, the back transition plug is tapered from the proximal to distal ends thereof.

In aspects according to the present disclosure, the back transition plug includes one or more mechanical interfaces configured to securely engage a corresponding mechanical interface disposed on the proximal link. In other aspects according to the present disclosure, the one or more mechanical interfaces includes a pair of opposing fingers that are configured to mechanically engage a corresponding pair of opposing recesses defined in the proximal link.

In aspects according to the present disclosure, the articulating electrosurgical instrument further includes a seal clip operably coupled to the distal end of the elongated shaft, the seal clip including a pair of opposing fingers that are configured to securely engage a corresponding pair of opposing apertures defined in the back transition plug.

In aspects according to the present disclosure, the articulating electrosurgical instrument further includes a seal disposed atop the seal clip between a proximal end of the back transition plug, the seal configured to seal the wrist assembly to the elongated shaft.

In aspects according to the present disclosure, the back transition plug is configured to guide a plurality of actuation cables therethrough to the wrist assembly, the plurality of actuation cables configured to articulate the end effector assembly upon translation thereof. In other aspects according to the present disclosure, the back transition plug includes a corresponding plurality of apertures defined therethrough to guide the plurality of articulation cables to the wrist assembly.

Provided in accordance with additional aspects of the present disclosure is an articulating electrosurgical instrument including a housing having an elongated shaft extending therefrom, the shaft defining a longitudinal axis therethrough and a wrist assembly operably supported to a distal end of the elongated shaft and configured to support an end effector assembly at distal end thereof. The end effector includes first and second jaw members, one or both of the first or second jaw members moveable relative to one another upon actuation of a cam rod disposed through the elongated shaft. The cam rod includes a cam member secured to a distal end thereof, the cam member configured to operably engage a cam slot defined within a proximal jaw flange of the movable jaw member to move the one or more jaw members upon translation thereof, wherein the cam member includes a crimp that is configured to secure the cam member to the cam rod.

In aspects according to the present disclosure, the crimp includes a geometric configuration configured to define a relief between the distal end of the cam member and the crimp, the relief allowing the cam member to pivot at an angle relative to the longitudinal axis. In other aspects according to the present disclosure, the geometric configuration is hexagonal.

In aspects according to the present disclosure, the cam member is configured to pivot when the cam member is pulled to a proximal portion of the slot defined in the movable jaw member.

In aspects according to the present disclosure, the relief is configured to eliminate potential catch points between the cam member and a transition between a distal segment and transition plug of the wrist assembly and allowing the cam member to pivot at an angle relative to the longitudinal axis during proximal translation of the cam member.

In aspects according to the present disclosure, the cam rod includes an outer tube disposed thereabout configured to increase rigidity of the cam rod and facilitate translation of the cam rod through the elongated shaft and the wrist assembly.

In aspects according to the present disclosure, the cam rod includes an outer tube disposed thereabout configured to reduce buckling of the cam rod when transitioning through the elongated shaft, wrist assembly and the end effector assembly. In other aspects according to the present disclosure, the outer tube is made from a superelastic or shape memory alloy.

In aspects according to the present disclosure, the outer tube extends to a point proximate a distal end of the cam rod and wherein a distal end of the tube is partially received in a counterbore defined within the cam member. In aspects according to the present disclosure, a second crimp secures an end of the outer tube to the cam member.

In aspects according to the present disclosure, the cam member includes a pivot bar configured to engage the slot defined within the proximal flange of the at least one jaw member.

Provided in accordance with additional aspects of the present disclosure is an articulating electrosurgical instrument including a housing having an elongated shaft extending therefrom, the shaft defining a longitudinal axis therethrough and a wrist assembly operably supported to a distal end of the elongated shaft and configured to support an end effector assembly at distal end thereof. The end effector includes first and second jaw members, one or both of the first or second jaw members is moveable relative to one another upon actuation of a cam rod disposed through the elongated shaft. The cam rod includes a cam member configured to operably engage a cam slot defined within a proximal jaw flange of the moveable jaw member to move the jaw member upon translation thereof. The cam member includes a first crimp configured to secure the cam member to the cam rod and the cam rod includes an outer tube disposed thereabout configured to facilitate translation of the cam rod through the elongated shaft and the wrist assembly. A distal end of the outer tube is secured within a counterbore defined within the cam member by a second crimp.

In aspects according to the present disclosure, the outer tube is made from a superelastic or shape memory alloy.

In aspects according to the present disclosure, the first crimp includes a geometric configuration configured to define a relief between the distal end of the cam member and the first crimp, the relief allowing the cam member to pivot at an angle relative to the longitudinal axis. In aspects according to the present disclosure, the geometric configuration is hexagonal.

In aspects according to the present disclosure, the cam member is configured to pivot when the cam member is pulled to a proximal portion of the slot defined in the at least one jaw member.

In aspects according to the present disclosure, the relief is configured to eliminate potential catch points between the cam member and a transition between a distal segment and transition plug of the wrist assembly and allowing the cam member to pivot at an angle relative to the longitudinal axis during proximal translation of the cam member.

In aspects according to the present disclosure, the cam member includes a pivot bar configured to engage the slot defined within the proximal flange of the movable jaw member.

In aspects according to the present disclosure, the outer tube is configured to reduce buckling of the cam rod when transitioning through the elongated shaft and the wrist assembly.

Provided in accordance with additional aspects of the present disclosure is an articulating electrosurgical instrument including a housing having an elongated shaft extending therefrom defining a longitudinal axis therealong and a wrist assembly operably supported to a distal end of the elongated shaft and configured to support an end effector assembly at distal end thereof. The end effector includes a pair of first and second jaw members, one or both of the first and second jaw members is moveable relative to the other jaw member. The wrist assembly includes a proximal link operably coupled to the distal end of the elongated shaft, a distal link operably coupled to the end effector assembly, and a central link operably coupled between the proximal link and the distal link, the central link including opposing proximal flanges configured to operably couple to the proximal link and opposing distal flanges configured to operably couple to the distal link. The distal flanges of the center link are oriented normally relative to the longitudinal axis and in line with the first and second jaw members to eliminate obstructing the view of the first and second jaw members during movement thereof.

In aspects according to the present disclosure, the proximal flanges are oriented transversely relative to the longitudinal axis.

In aspects according to the present disclosure, one or both of the distal or proximal pair of flanges of the central link includes shoulders configured to facilitate rotational engagement with one or both of the proximal and distal links. In other aspects according to the present disclosure, the shoulders are recessed relative to a distal end of the respective flange. In yet other aspects according to the present disclosure, each shoulder includes a radius of curvature to control the relative rotation between adjacent links.

In aspects according to the present disclosure, the distal pair of flanges of the central link include first shoulders and the proximal pair of flanges of the central link include second shoulders, the first and second shoulders cooperating to facilitate rotational engagement with respective the distal and proximal links.

In other aspects according to the present disclosure, the first and second shoulders include radiuses of curvature to control the relative rotation between respective adjacent links. In still other aspects according to the present disclosure, the radius of curvature of the first shoulders differs from the radius of curvature of the second shoulders. In yet other aspects according to the present disclosure, one (or more) of radiuses of curvature of the first or second shoulders is varied along the length thereof to reduce the possibility of tissue pinching between respective adjacent links.

Provided in accordance with additional aspects of the present disclosure is an articulating electrosurgical instrument including a housing having an elongated shaft extending therefrom defining a longitudinal axis therealong and a wrist assembly operably supported to a distal end of the elongated shaft and configured to support an end effector assembly at distal end thereof. The end effector includes a pair of first and second jaw members, one or both of the first and second jaw members is moveable relative to the other jaw member. The wrist assembly includes a central link operably disposed between a proximal link and distal link, the central link including shoulders including respective radiuses of curvature to control the relative rotation between adjacent proximal and distal links. One or more of the radiuses is configured to allow over-travel between respective adjacent proximal and distal links.

In aspects according to the present disclosure, the shoulders are configured to facilitate rotational engagement with the proximal and distal links. In other aspects according to the present disclosure, the radius of curvature of the shoulders between the proximal link and the central link differs from the radius of curvature of the shoulders between the distal link and the central link.

In aspects according to the present disclosure, one or more of the radiuses of curvature of the shoulders between the proximal link and the central link and the distal link and the central link varies along a length thereof to reduce the possibility of tissue pinching between respective adjacent links.

In aspects according to the present disclosure, the center link includes a pair of distal flanges configured to engage the distal link, the distal flanges of the central link oriented normally relative to the longitudinal axis and in-line with the first and second jaw members to eliminate obstructing the view of the first and second jaw members during movement thereof. In other aspects according to the present disclosure, the shoulders are disposed on the distal flanges of the central link. In still aspects according to the present disclosure, the shoulders are recessed relative to a distal end of the distal flanges of the central link.

In aspects according to the present disclosure, the center link includes a pair of distal flanges configured to engage the distal link and a pair of proximal flanges configured to engage the proximal link.

In aspects according to the present disclosure, the proximal flanges of the central link are oriented transversely relative to the longitudinal axis and the distal flanges are oriented normally relative to the longitudinal axis and in line with the first and second jaw members to eliminate obstructing the view of the first and second jaw members during movement thereof. In aspects according to the present disclosure, the shoulders are disposed on the distal and proximal flanges of the central link.

Provided in accordance with additional aspects of the present disclosure is an articulating electrosurgical instrument including a housing having an elongated shaft extending therefrom, the elongated shaft defining a longitudinal axis therethrough and a wrist assembly operably supported to a distal end of the elongated shaft and configured to support an end effector assembly at distal end thereof. The end effector includes first and second jaw members, one or both of the first or second jaw members is moveable relative to one another upon actuation of a cam rod disposed through the elongated shaft. The cam rod includes a cam member secured to a distal end thereof having a pivot rod extending therefrom. The pivot rod is configured to operably engage one or more cam slots defined within a proximal jaw flange of the one or more jaw members to move the one or more jaw members upon translation thereof. The cam member includes a weld bore defined therein configured to facilitate securing the pivot rod to the cam member.

In aspects according to the present disclosure, the pivot rod extends transversely from the cam member relative to the longitudinal axis.

In aspects according to the present disclosure, the one or more jaw members includes a proximal flange that is bifurcated to include two cam slots defined therein and the pivot rod extends transversely from the cam member relative to the longitudinal axis to engage the two cam slots.

In aspects according to the present disclosure, the weld bore is configured to facilitate welding the pivot rod to the cam member.

In aspects according to the present disclosure, the weld bore is centered on the cam member or in a direction along the pivot rod axis to ensure proper loading of the pivot rod within the cam member.

Provided in accordance with additional aspects of the present disclosure is a method of assembling an articulating electrosurgical instrument including: engaging an elongated shaft to a housing, the elongated shaft defining a longitudinal axis therethrough; engaging a wrist assembly to a distal end of the elongated shaft, the wrist assembly configured to support an end effector assembly at distal end thereof, the wrist assembly including a central link operably disposed between a proximal link and distal link; feeding a cam rod through the elongated shaft, the proximal link, the center link and the distal link; securing a cam member to a distal end of the cam rod; and operably coupling the end effector assembly to the cam member and the distal link.

In aspects according to the present disclosure, the cam rod is flexible. In other aspects according to the present disclosure, the cam rod is fed through respective passageways defined within the proximal link, center link and distal link.

In aspects according to the present disclosure, securing the cam member to the cam rod includes crimping. In other aspects according to the present disclosure, securing the cam member to the cam rod includes crimping with a geometrical cross section.

In aspects according to the present disclosure, prior to operably coupling the end effector assembly to the cam member, the method further includes operably engaging a pivot rod to the cam member. In other aspects according to the present disclosure, the pivot rod extends transversely from the cam member relative to the longitudinal axis.

In aspects according to the present disclosure, operably engaging the pivot rod to the cam member includes welding. In other aspects according to the present disclosure, welding includes welding the pivot rod to the cam member through a weld bore defined within the cam member. In aspects according to the present disclosure, the weld bore is centrally disposed in the cam member or in a direction along the pivot rod axis to ensure proper loading of the pivot rod within the cam member.

In aspects according to the present disclosure, operably coupling the end effector assembly to the cam member includes coupling the pivot rod to corresponding slots defined in a proximal end of a jaw member of the end effector assembly.

In aspects according to the present disclosure, the cam rod is fed through the respective passageways defined in the proximal, central and distal links.

In aspects according to the present disclosure, the end effector assembly includes first and second jaw members each having proximal flanges extending therefrom and wherein operably coupling the end effector assembly to the distal link includes engaging a transition plug of the wrist assembly with the proximal flanges of the first and second jaw members of the end effector assembly.

In aspects according to the present disclosure, a transition lumen extends through the proximal link, central link and distal link and wherein the transition lumen includes a passageway defined therethrough configured to receive the cam rod for translation therein.

BRIEF DESCRIPTION OF THE DRAWINGS

Various aspects and features of the present disclosure are described hereinbelow with reference to the drawings wherein.

DETAILED DESCRIPTION

Figure 1:
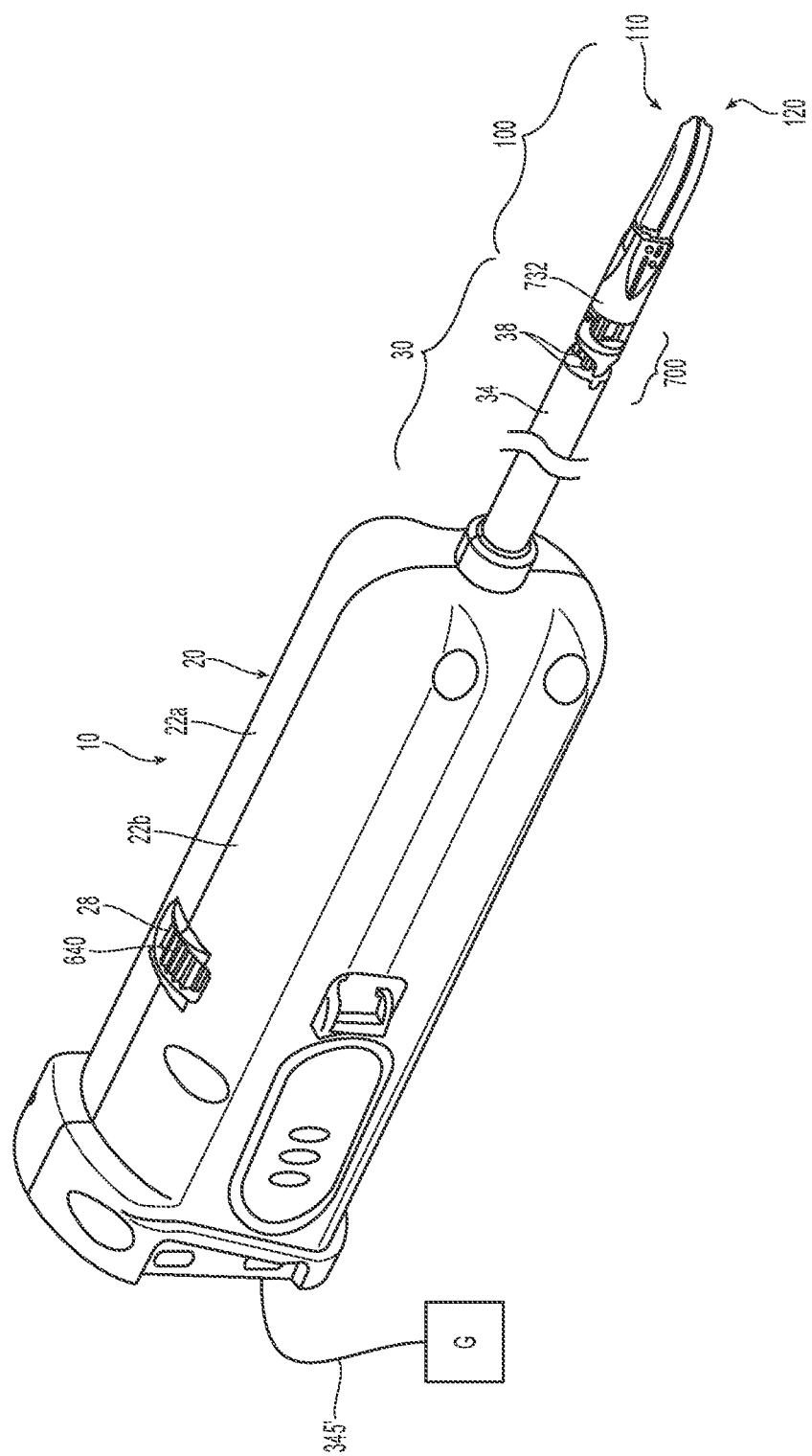
FIG. 1 is a perspective view of a surgical instrument in accordance with the present disclosure configured for mounting on a robotic arm of a robotic surgical system.
Figure 2:
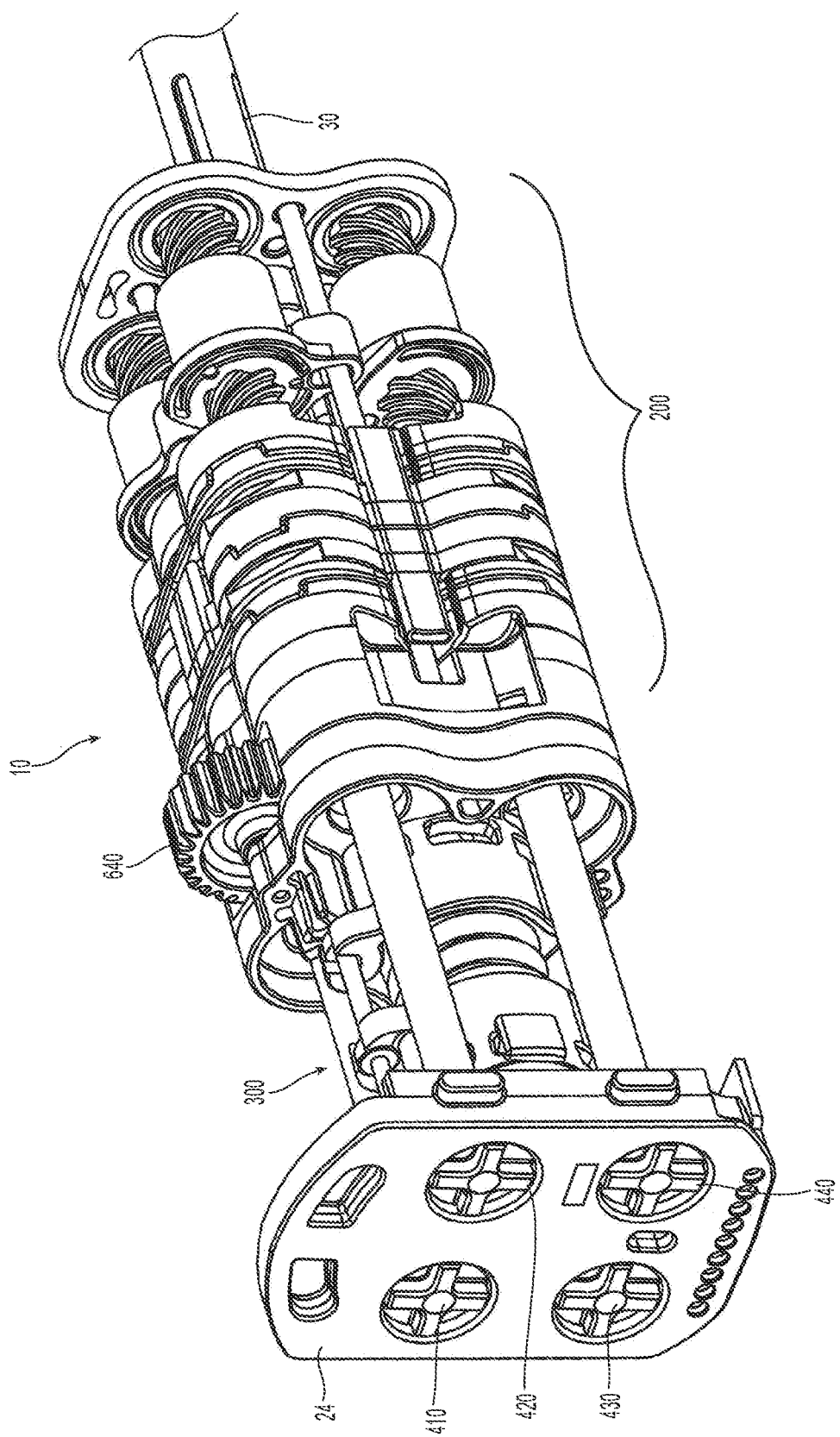
FIG. 2 is a rear perspective view of a proximal portion of the surgical instrument of FIG. 1 with an outer housing removed.
Figure 3:
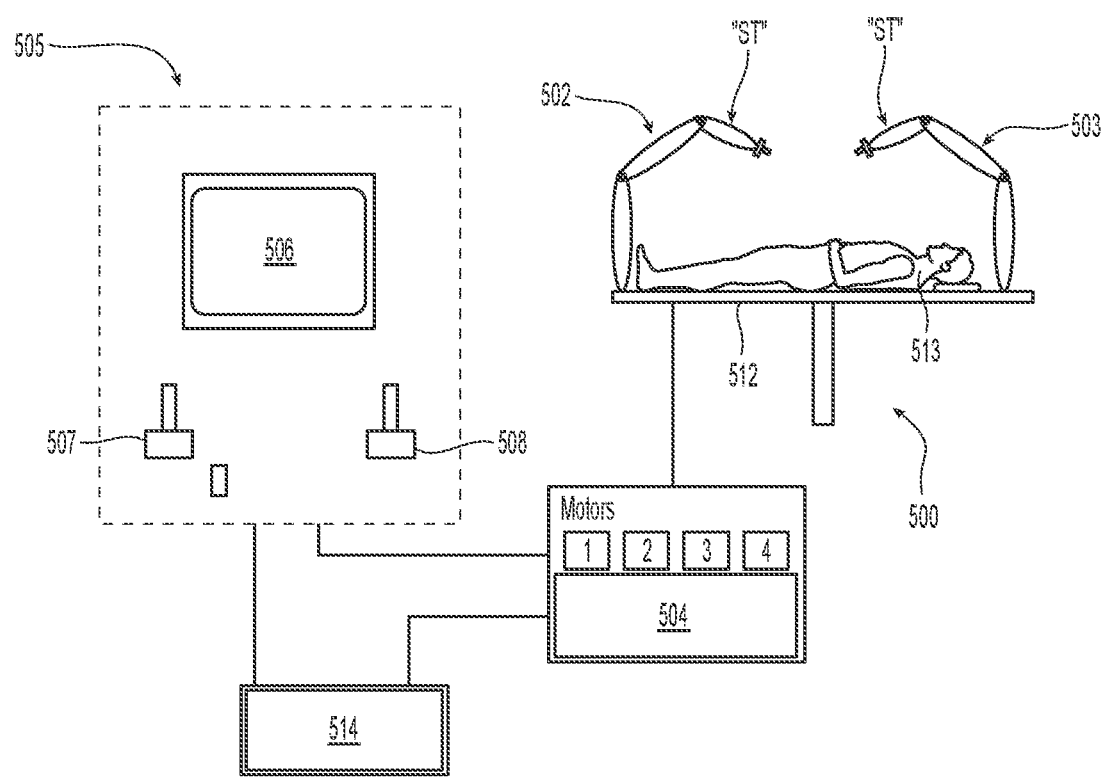
FIG. 3 is a schematic illustration of an exemplary robotic surgical system configured to releasably receive the surgical instrument of FIG. 1.

Referring to FIGS. 1 and 2, a surgical instrument 10 provided in accordance with the present disclosure generally includes a housing 20, a shaft 30 extending distally from the housing 20, an end effector assembly 100 extending distally from the shaft 30, and an actuation assembly 300 disposed within the housing 20 and operably associated with the shaft 30 and the end effector assembly 100. The surgical instrument 10 is detailed herein as an articulating electrosurgical forceps configured for use with a robotic surgical system, e.g., robotic surgical system 500 (FIG. 3). However, the aspects and features of the surgical instrument 10 provided in accordance with the present disclosure, detailed below, are equally applicable for use with other suitable surgical instruments (including non-robotic surgical instrument) and/or in other suitable surgical systems (including non-robotic surgical systems).

The housing 20 of the surgical instrument 10 includes first and second body portions 22a, 22b and a proximal faceplate 24 (FIG. 2) that cooperate to enclose the actuation assembly 300 therein. The proximal faceplate 24 includes apertures defined therein through which inputs 410, 420, 430, 440 of the actuation assembly 300 extend. A pair of latch levers extends outwardly from opposing sides of the housing 20 and enables releasable engagement (directly or indirectly) of the housing 20 with a robotic arm of a surgical system, e.g., robotic surgical system 500 (FIG. 3). An aperture 28 defined through the housing 20 permits a thumbwheel 640 to extend therethrough to enable manual manipulation of the thumbwheel 640 from the exterior of the housing 20 to permit manual opening and closing of the end effector assembly 100.

The shaft 30 of the surgical instrument 10 includes a distal segment 732 (such as, for example, a collar or clevis), a proximal segment 34, and an articulating assembly 700 disposed between the distal and proximal segments 732, 34, respectively. The articulating assembly 700 includes one or more articulating components, e.g., links, joints, etc. Details relating to the articulating assembly are explained in more detail below with reference to FIGS. 4A-10B. A plurality of articulation cables 738a and 738b, e.g., four (4) articulation cables, or other suitable actuators, extends through the articulating assembly 700. More specifically, the articulation cables 738a and 738b are operably coupled to the distal segment 732 of the shaft 30 at the distal ends thereof and extend proximally from the distal segment 732 of the shaft 30, through the articulating assembly 700 and the proximal segment 34 of the shaft 30, and into the housing 20, wherein the articulation cables 738a and 738b operably couple with an articulation actuator 200 of the actuation assembly 300 to enable selective articulation of the distal segment (and, thus the end effector assembly 100) relative to the proximal segment 34 and the housing 20, e.g., about at least two axes of articulation (yaw and pitch articulation, for example). The articulation actuator 200 is operably coupled between the first and second inputs 410, 420, respectively, of the actuation assembly 300 and the articulation cables 738a, 738b (FIG. 1) such that, upon receipt of appropriate rotational inputs into the first and/or second inputs 410, 420, the articulation actuator 200 manipulates the articulation cables 738a, 738b to articulate the end effector assembly 100 in a desired direction, e.g., to pitch and/or yaw the end effector assembly 100. The articulation cables 738a, 738b are arranged in a generally rectangular configuration, although other suitable configurations are also contemplated.

With respect to articulation of the end effector assembly 100 relative to the proximal segment 34 of the shaft 30, actuation of the articulation cables 738a, 738b is effected in pairs. More specifically, in order to pitch the end effector assembly 100, the upper pair of cables 738 is actuated in a similar manner while the lower pair of cables 738a, 738b is actuated in a similar manner relative to one another but an opposite manner relative to the upper pair of cables 738a, 738b. With respect to yaw articulation, the right pair of cables 738a, 738b is actuated in a similar manner while the left pair of cables 738a, 738b is actuated in a similar manner relative to one another but an opposite manner relative to the right pair of cables 738a, 738b. More details relating to the articulation cable are discussed below with respect to FIGS. 9B and 9C.

Turning now to FIG. 3, a robotic surgical system 500 is configured for use in accordance with the present disclosure. Aspects and features of the robotic surgical system 500 not germane to the understanding of the present disclosure are omitted to avoid obscuring the aspects and features of the present disclosure in unnecessary detail.

The robotic surgical system 500 generally includes a plurality of robot arms 502, 503; a control device 504; and an operating console 505 coupled with control device 504. The operating console 505 may include a display device 506, which may be set up in particular to display three-dimensional images; and manual input devices 507, 508, by means of which a person, e.g., a surgeon, may be able to telemanipulate the robot arms 502, 503 in a first operating mode. The robotic surgical system 500 may be configured for use on a patient 513 lying on a patient table 512 to be treated in a minimally invasive manner. The robotic surgical system 500 may further include a database 514, in particular coupled to the control device 504, in which are stored, for example, pre-operative data from the patient 513 and/or anatomical atlases.

Each of the robot arms 502, 503 may include a plurality of members, which are connected through joints, and a mounted device which may be, for example, a surgical tool "ST." One or more of the surgical tools "ST" may be the surgical instrument 10 (FIG. 1), thus providing such functionality on a robotic surgical system 500.

Specifically, the actuation assembly 300 (FIG. 2) is configured to operably interface with the robotic surgical system 500 when the surgical instrument 10 is mounted on the robotic surgical system 500 to enable robotic operation of the actuation assembly 300. That is, the robotic surgical system 500 selectively provides rotational inputs to inputs 410, 420, 430, 440 of the actuation assembly 300 to articulate the end effector assembly 100, grasp tissue between the first and second jaw members 110, 120, and/or cut tissue grasped between the first and second jaw members 110, 120.

The robot arms 502, 503 may be driven by electric drives, e.g., motors, connected to the control device 504. The control device 504, e.g., a computer, may be configured to activate the motors, in particular by means of a computer program, in such a way that the robot arms 502, 503, and, thus, their mounted surgical tools "ST" execute a desired movement and/or function according to a corresponding input from the manual input devices 507, 508, respectively. The control device 504 may also be configured in such a way that it regulates the movement of the robot arms 502, 503 and/or of the motors.

Figure 4A:
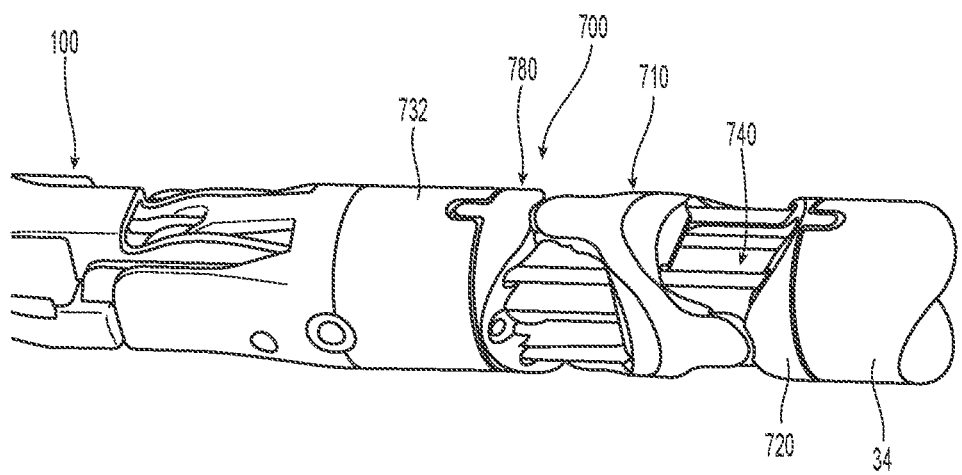
FIG. 4A is a side view of a wrist assembly for use with the surgical instrument of FIG. 1.
Figure 4B:
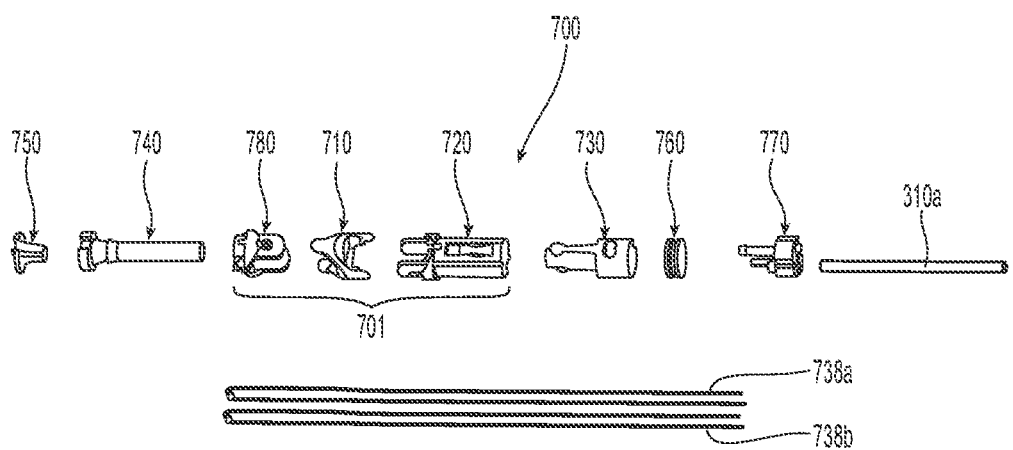
FIG. 4B is an exploded view of the wrist assembly of FIG. 4A.

Turning to FIGS. 4A-10B, details relating to the articulation assembly 700 are shown and described herein. More particularly and as shown in FIGS. 4A and 4B, articulation assembly 700 generally includes a front transition plug 750, a transition lumen 740, a distal link 780, a center link 710, a proximal link 720, a back transition plug 730, a seal 760, and a seal clip 770. The actuation cables 738a, 738b and a cam or drive rod 310a (or drive push/pull cable, e.g., stranded cable assembly including a Nitinol® outer tube to prevent buckling) extend through the articulation assembly 700 as explained in detail below. Collectively, the distal link 780, the central link 710 and the proximal link 720 and other external and internal components therein collectively make up the so-called "wrist assembly" 701. FIG. 4A shows the articulation assembly 700 assembled for use and FIG. 4B shows an exploded view of the articulation assembly 700 with the various above-mentioned components separated.

Front transition plug 750 shown in FIGS. 5A-5D is configured to facilitate transitioning of the cam rod 310a and electrical leads 345a, 345b (FIGS. 5C, 5D and 6F) into the end effector assembly 100. Front transition plug 750 is generally mushroom-shaped to include a cap 751 and a stem 756 that depends therefrom, the stem 756 is configured for insertion within a distal end of the transition lumen 740. A central passage 753 is defined through the plug 750 that is configured to receive the cam rod 310a for reciprocation therein. A second, transitional passageway 756a (may be S-shaped) is defined through the plug 750 and is configured to facilitate transition and reciprocation of the blade rod 350 (FIGS. 6B, 7D) therein via blade actuator or input 430 (FIG. 1). A pair of relief channels 752a, 752b (FIG. 5D) is defined in the distal surface of the plug 750 and is configured to seat the flanges 124 (FIG. 6F) of fixed jaw member 120 providing lateral stability and rotational clearance for the end effector assembly 100. A key notch 757 (FIG. 5D) is defined in the distal surface of the plug 750 and is configured to secure a keying feature of distal segment 732 (FIG. 4A) providing par clocking/alignment and lateral stability to the end effector assembly 100.

A cut-out 755 is defined in cap 751 (FIG. 5D) to facilitate passage of electrical leads 345a, 345b from the transition lumen 740 and into the end effector assembly 100. More particularly, leads 345a, 345b are configured to navigate internally through the transition lumen 740 and along the outer peripheral surface of stem 756 and through cut-out 755 into the end effector assembly 100. Leads 345a, 345b may be configured to travel along a helical path through the transition lumen 740 and into the plug 750 to reduce strain or unintended tension on the leads 345a, 345b during articulation and allow for a smoother transition to the end effector assembly 100. One or more mechanical interfaces, e.g., tangs 759, facilitate coupling and securing the plug 750 within the transition lumen 740. In embodiments, plug 750 and lumen 740 may be integrally formed.

Figure 6A:
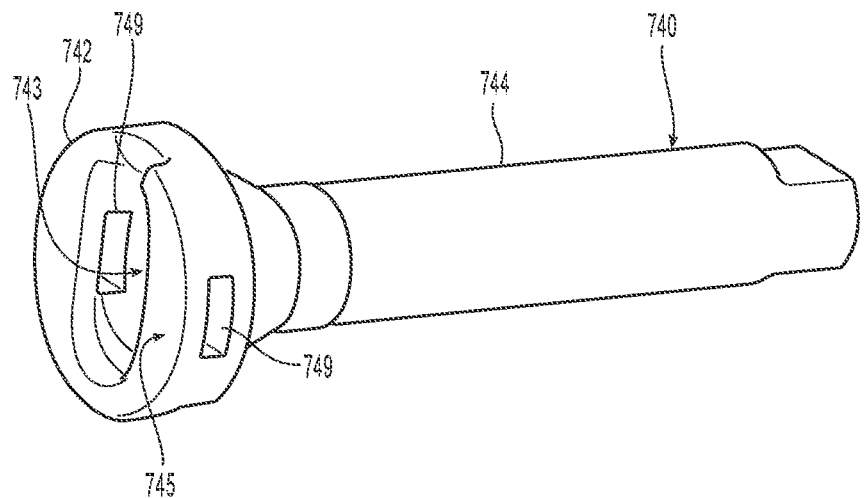
FIGS. 6A-6F are various views of a transition lumen of the wrist assembly of FIG. 4A.

As mentioned above, plug 750 is configured for insertion within the transition lumen 740 wherein the stem 756 of the plug 750 is secured therein while the cap 751 abuts the end effector assembly 100. Once completely inserted, tangs 759 engage complementary surfaces 749 of the transition lumen to secure the plug 750 within the transition lumen 740 (FIG. 6A). When inserted, the proximal portion of the plug 750 is compressed into a generally frustoconical configuration within the lumen 740. When operably coupled within the lumen 740, the helical pathway 756a of the plug 750 aligns with the internal helical pathway 741 of the lumen 740 to facilitate reciprocation of the blade rod 350 by reducing unintended motions at the end effector due to opening of the jaw members 110, 120 or reciprocation of the blade rod 350 and/or by reducing any strain due to articulation as explained in more detail below.

Figure 5A:
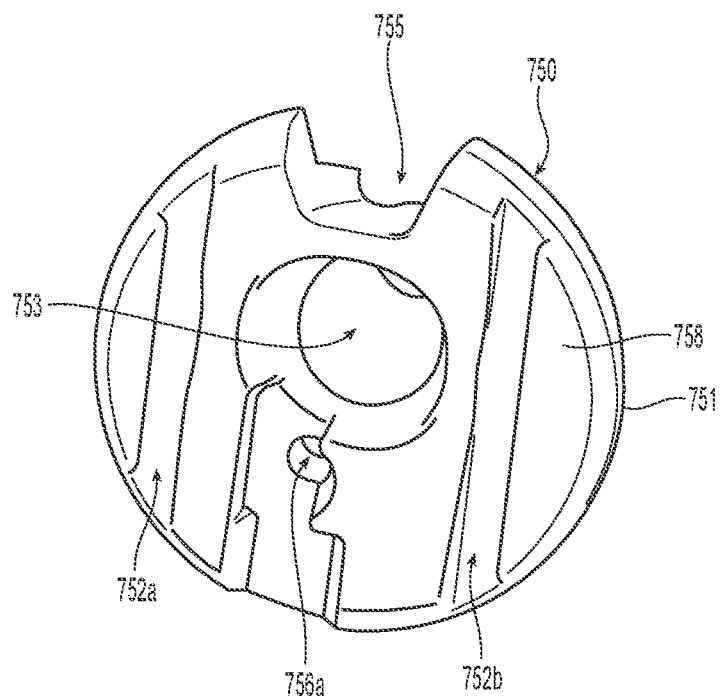
FIGS. 5A-5D are various views of a transition plug of the wrist assembly of FIG. 4A.
Figure 5B:
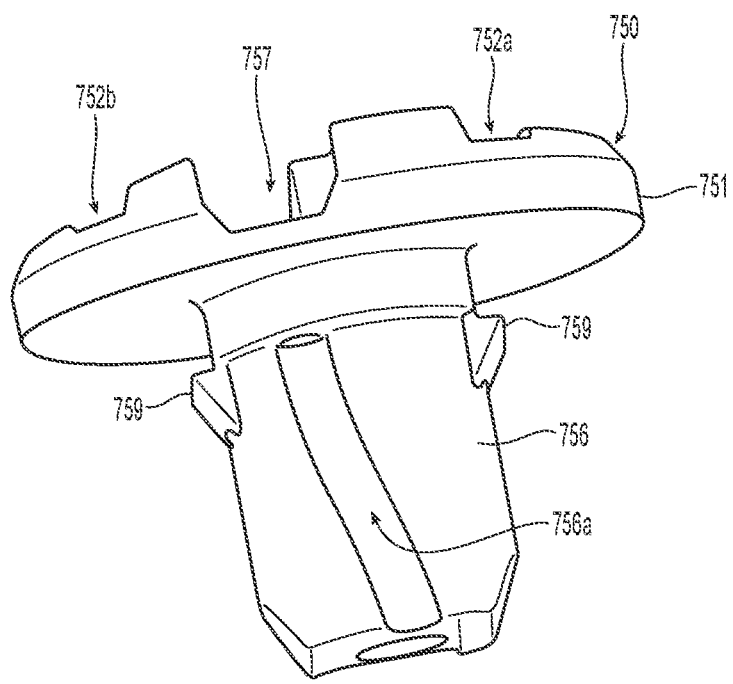
Figure 5C:
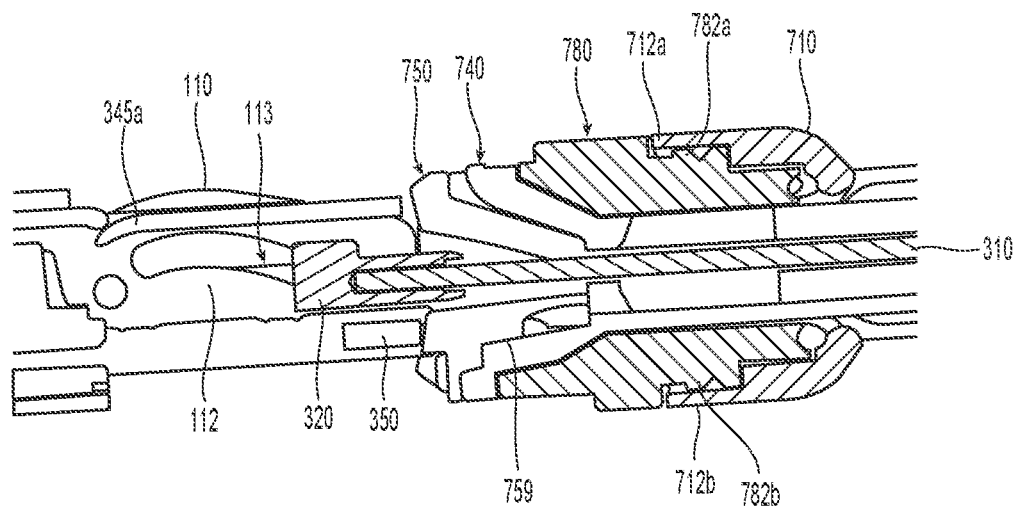
Figure 5D:
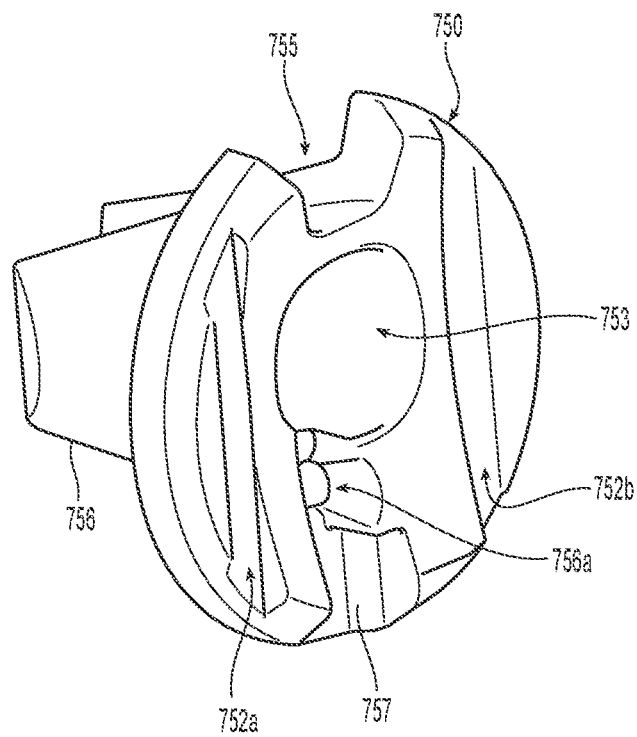

Turning in detail to FIGS. 6A-6F, transition lumen 740 is typically made from a rubber-like material or moldable thermoplastic polyurethane, e.g., pellethane, pelathyane (urethane) or the like, and includes a cap 742 and an elongated stem 744 trailing therefrom. Lumen 740 includes an internal, generally central, passage 743 used to reciprocate the cam or drive rod 310a therein that is disposed in longitudinal registration with passageway 753 of plug 750. Likewise, a helical pathway 741 (FIG. 6D) extends therethrough and includes a distal end that is disposed in registration with helical pathway 756a of plug 750 (FIG. 5B). Helical pathway 741 is configured to smoothly reciprocate the blade rod 350 therein regardless of the articulation angle of the end effector 100 as explained in more detail below. A lead passageway 748 (FIG. 6C) is also defined in the transition lumen 740 and is configured to guide the lead wires 345a, 345b from the elongated shaft 30, into plug 750 and into the end effector assembly 100.

Figure 6B:
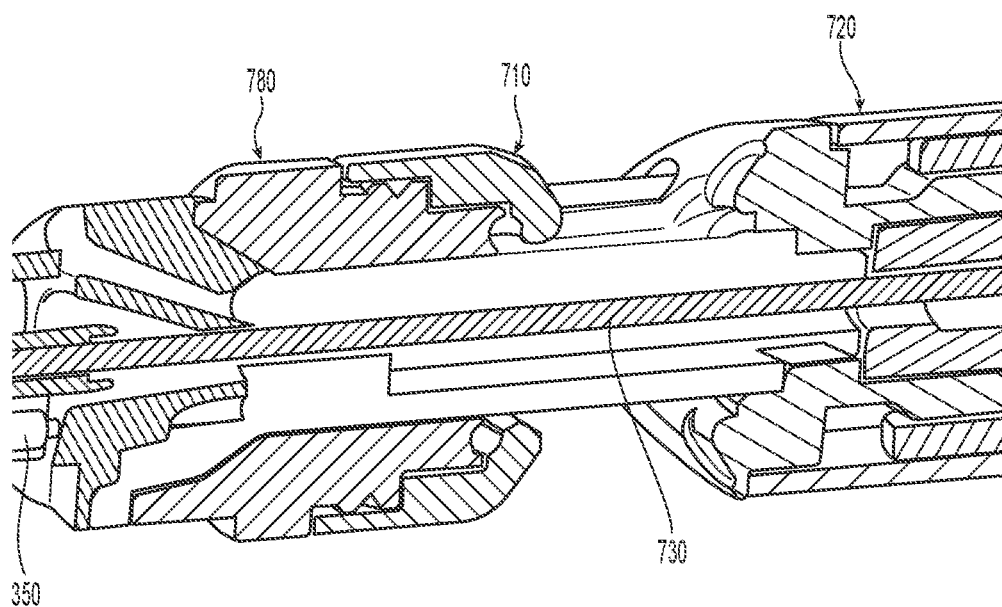
Figure 6C:
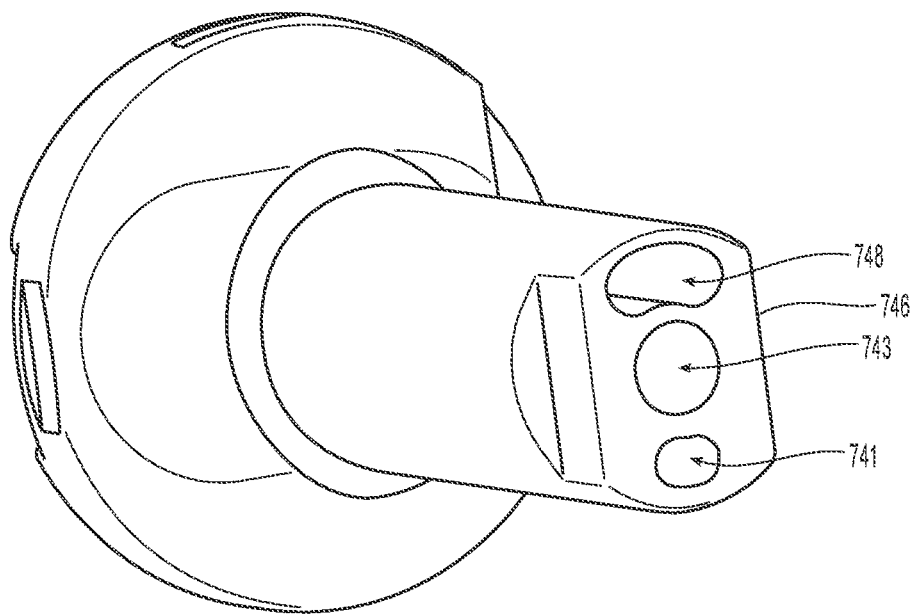
Figure 6D:
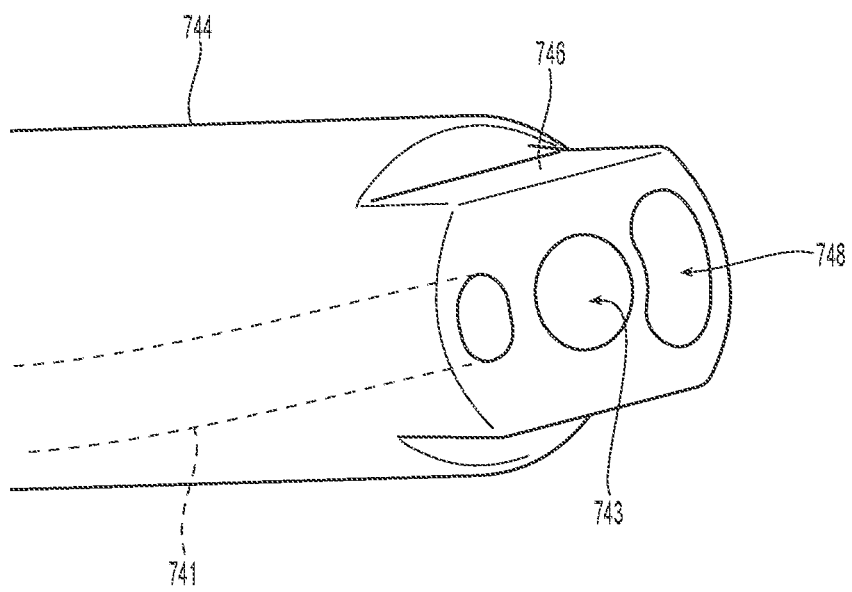
Figure 6E:
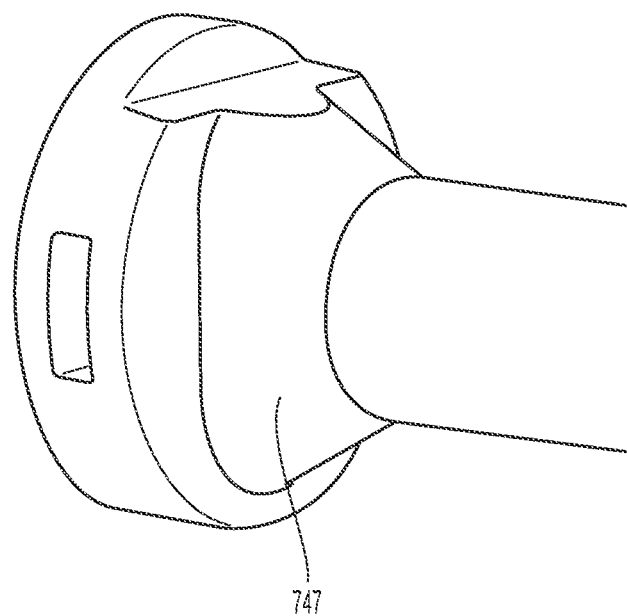
Figure 6F:
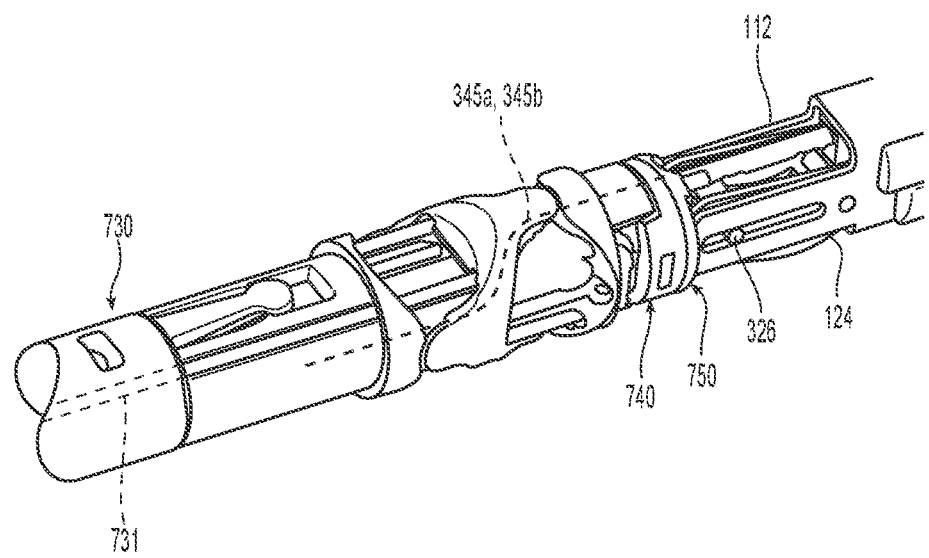

The proximal end 746 of the lumen 740 is keyed to align and ensure proper engagement with proximal link 720 and reduce friction losses through the lumen 740 as the blade rod 350 and cam rod 310a reciprocate through the articulation assembly 700 (FIGS. 6B and 6D). The proximal end of the cap 742 also includes a taper 747 (FIG. 6E) extending to the stem 744 to facilitate engagement within distal link 780 and to guide the lead wires 345a, 345b through the lumen 740 from the proximal to distal ends and into plug 750 (FIG. 6F).

Figure 7A:
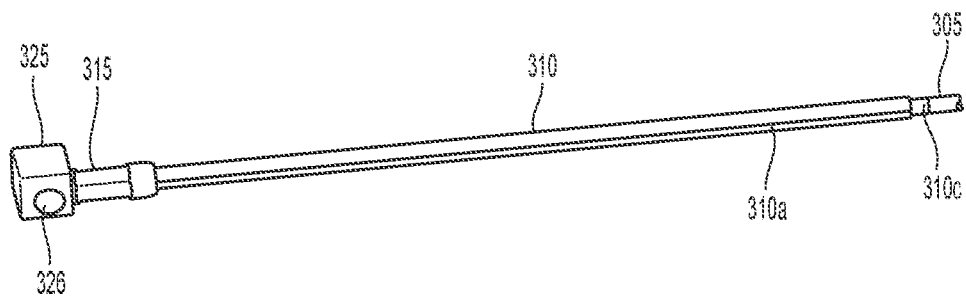
FIGS. 7A-7F are various views of a cam rod and camming member which are configured to translate within the wrist assembly upon actuation thereof.
Figure 7B:
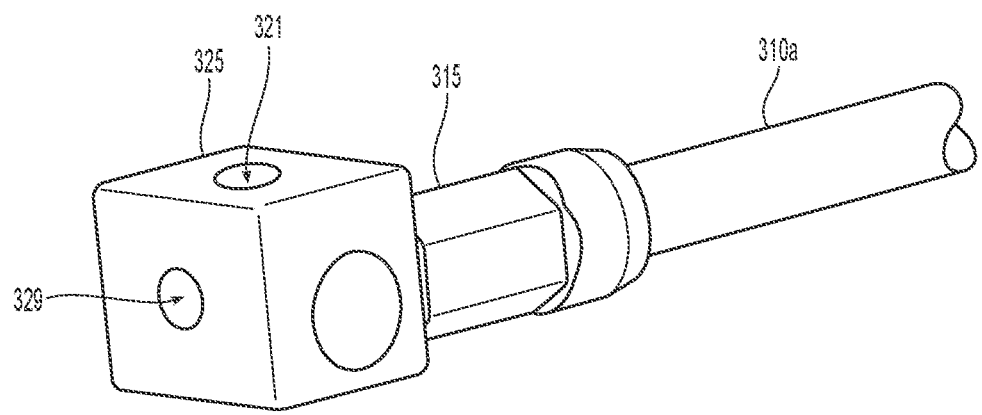
Figure 7C:
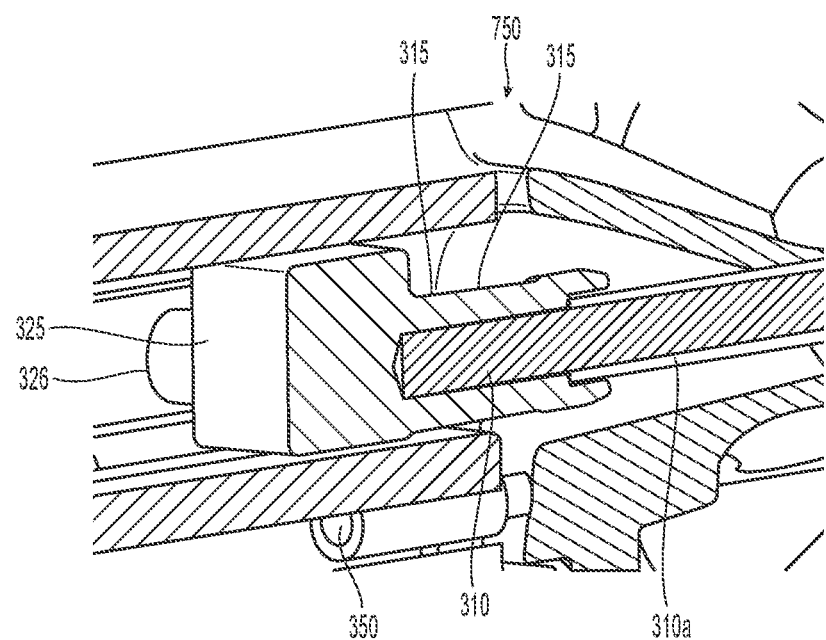
Figure 7D:
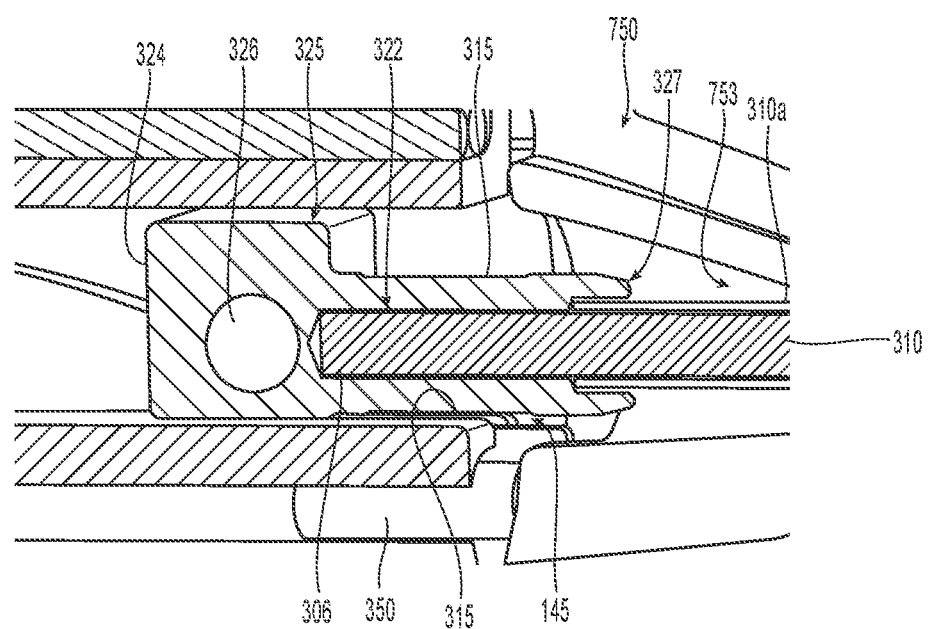
Figure 7E:
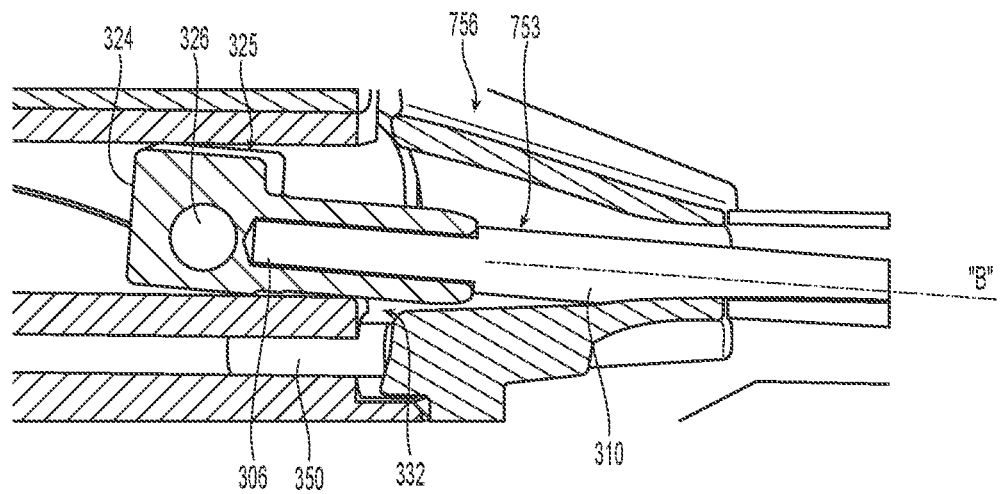

Turning now to FIGS. 7A-7F, the cam rod 310a is shown alone (FIGS. 7A and 7B) and shown from various angles engaged within the articulation assembly 700 (FIGS. 7C-7F). More particularly, cam rod 310a includes a proximal end 305 that is configured to engage the actuation assembly 300 and a distal end 306 that is configured to engage a crimp 315 of a cam member 325 (FIGS. 7C-7E). A pivot rod 326 (or cam driving pin or cam driving boss) extends transversally through (or may be configured to project transversally from, e.g., pivot boss) the cam member 325 and is configured to operably engage a corresponding cam slot 113 defined in the flange 112 of jaw member 110 (FIG. 5C) (and cam slot in jaw member 120 (not shown)) such that movement of the cam rod 310a through the articulation assembly 700 pivots the jaw members 110, 120 between the open and closed positions. Flange 112 may be bifurcated to include two cam slots 113 for engagement with the pivot rod 326 on either side of the cam member 325, i.e., transversely.

Cam rod 310a may be made from stainless steel or any other type of flexible and strong material that can absorb the necessary strains and stresses associated with camming the jaw members 110, 120, e.g., stranded cable. A Nitinol® tube 310 may be disposed over the cam rod 310a to increase rigidity and to provide a smoother surface area for translation through the lumen 740 (FIGS. 7B-7E). Surgical grease may be utilized with the Nitinol® tube 310 or other tubes of tubes. Alternatively, a coating, e.g., a polyamide, may be extruded atop the cam rod 310a or otherwise deposited thereon to increase rigidity, support compressive loads and facilitate translation through the lumen 740. A polyamide coating provides smoother push/pull translation without the need for surgical grease. Any of the components describes herein can include a polyamide or similar coating to reduce wear for friction. Lubricants or other coating and/or surface treatments may be included in lieu of or in addition to a polyamide material to coat any of the components described herein to limit friction and component wear. A crimp 310c may be utilized to retain Nitinol® tube 310 atop cam rod 310a.

FIGS. 7D and 7E show a detailed view of the internal connection of the cam rod 310a to the cam member 325. More particularly, the distal end 306 of the cam rod 310a is configured to be received within an elongated channel 322 defined within the cam member 325. The proximal end of the elongated channel 322 includes a counter bore 327 defined therein which is configured to receive the outer Nitinol® tube 310, or coating, when the cam rod 310a is fully inserted within the elongated channel 322. Once inserted, the cam member 325 is crimped to mechanically retain the cam rod 310a therein. A hex-like or other geometrically-shaped similar type crimp 315 is formed on the outer peripheral surface of the cam member 325 to allow the cam member 325 freedom to pivot or deflect at an angle β" relative to a longitudinal axis defined through the elongated shaft 30 during proximal translation of the cam member 325 at a point 332 proximate a relief 145 defined by the distal end 324 of the cam member 325 and the crimp 315 between the plug 750 and the end effector assembly 100 (FIGS. 7D and 7E). Moreover, the hex-like crimp 315 is oriented to eliminate any possible catch points between the cam member 325 and the transition between the distal segment 732 and the plug 750 and allow the cam member 325 to pivot at an angle "β" during proximal translation of the cam member 325.

Figure 7F:
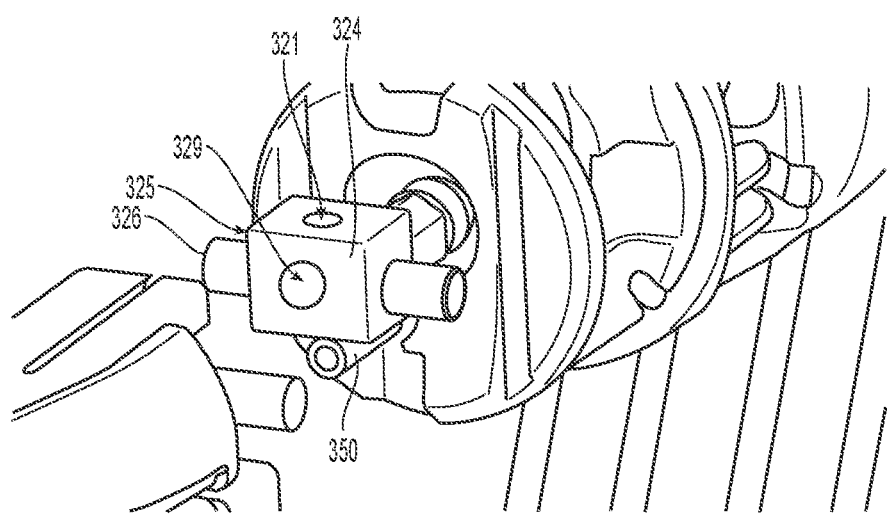

FIG. 7F shows a distal perspective view highlighting the cam rod 310a at assembly and showing a weld bore 329 defined in the distal-most surface or top surface 324 of the cam member 325. Weld bore 329 provides a point of access for welding the cam rod 326 to the cam member 325 during assembly. Providing the weld on center or along the pivot rod axis allows proper loading of the cam rod 326 and reduces weld splatter from reaching the bearing surfaces of the cam rod 326 which could affect performance of the cam rod 326. The weld bore 329 may remain open after welding or plugged as needed. Weld bore may also be defined within a different surface of the cam member 325, e.g., surface 321.

Turning now to FIGS. 8A-9D which shows the wrist link assembly 701 composed of the three links, e.g., distal articulation link 780, center articulation link 710 and proximal articulation link 720. A pair of opposing distal pivot flanges 712a, 712b disposed normal to a longitudinal axis "L" defined therethrough and a pair of proximal pivot flanges 711a, 711b disposed about ninety degrees (90°) offset from the distal flanges 712a, 712b. Each pair of opposing flanges defines a rotation plane, e.g., flanges 712a, 712b define a rotation plane transverse "T" to the longitudinal axis "L" and proximal flanges 711a, 711b define a rotation plane normal "N" to the longitudinal axis "L". The distal and proximal flanges 712a, 712b and 711a, 711b of the center link 710 are configured to reside in close proximity relative to one another to eliminate dead space along the articulation assembly 700. More specifically, center articulation link 710 includes pivot bearing surfaces 713a, 713b on the distal end and 717a, 717b on the proximal end. Each pair of bearing surfaces defines a theoretical pivot axis, PA1 and PA2, respectively. The wrist link assembly 701, and specifically the center link 710, is configured so the distance between these theoretical pivot axes PA1, PA2 are minimized. Minimizing the distance between the pivot axis PA1, PA2 reduces so called "dead space" along articulation assembly 700. Surfaces 711a, 711b and 712a, 712b are configured to both act as side bearing surfaces against bearings 721a and 721b (FIG. 9A) for alignment purposes and act as covers to prevent possible tissue pinch points.

Center link 710 is configured to mechanically couple to proximal link 720 at flanges 711a, 711b and distal link 780 at flanges 712a, 712b. Central link 710 includes various shoulders and additional structure (not explicitly shown) configured to facilitate rotational engagement with both links 780 and 720. For example, shoulders 713a, 713b are disposed proximate respective flanges 712a, 712b and may be configured to include a specific radius of curvature to control the relative rotation of the respective links, e.g., link 710 relative to link 780. Likewise, shoulders 717a, 717b are disposed proximate respective flanges 711a, 711b and may be configured to include a specific radius of curvature to control the relative rotation of the respective links, e.g., link 710 relative to link 720. Controlling the radius of curvature not only controls the degree of rotation of the respective links, e.g., link 710 relative to link 780 or link 710 relative to link 720, but may be engineered to reduce tissue pinch points 810 between the same. The radius of any of the shoulders 713a, 713b or 717a, 717b may be varied or different from the radii of the other shoulders to limit tissue pinch. Moreover, the center link 710 may be designed to over-travel to eliminate possible tissue pinch points.

Center link 710 also defines a passage 715 that is configured to pass the articulation cables 738a, 738b, leads 345a, 345b, cam rod 310a and blade rod 350 therethrough. Likewise, distal link 780 and proximal link 720 also include passageways, e.g., passageways 785, 728a, and 728b of distal link 780 and passageways 725 of proximal link 720, respectively, configured to pass the articulation cables 738a, 738b, leads 345a, 345b, cam rod 310a and blade rod 350 therethrough.

Figure 8A:
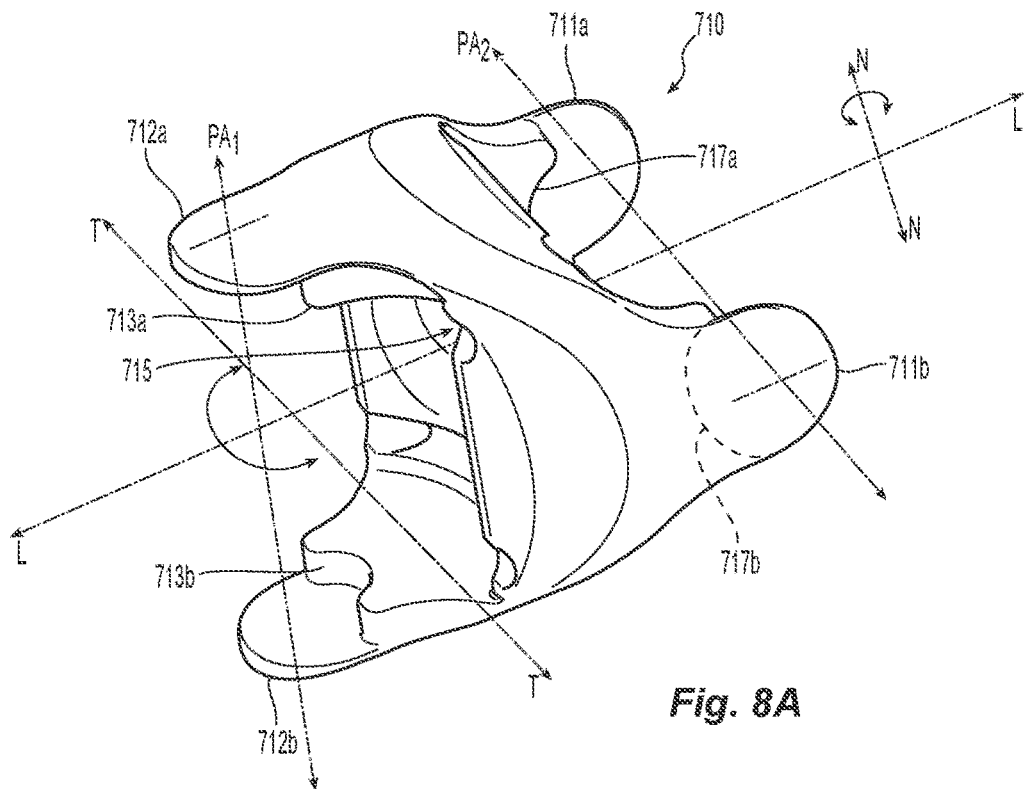
FIGS. 8A-8C are various views of a center link and distal link of the wrist assembly of FIG. 4A.
Figure 8B:
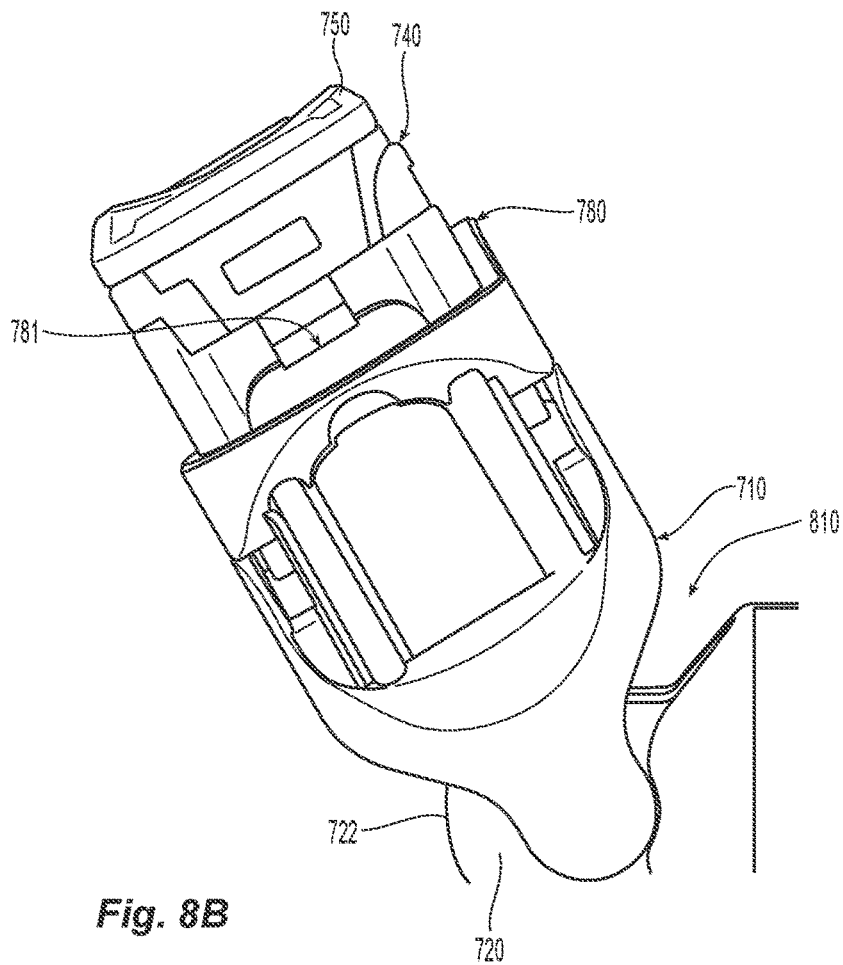
Figure 8C:
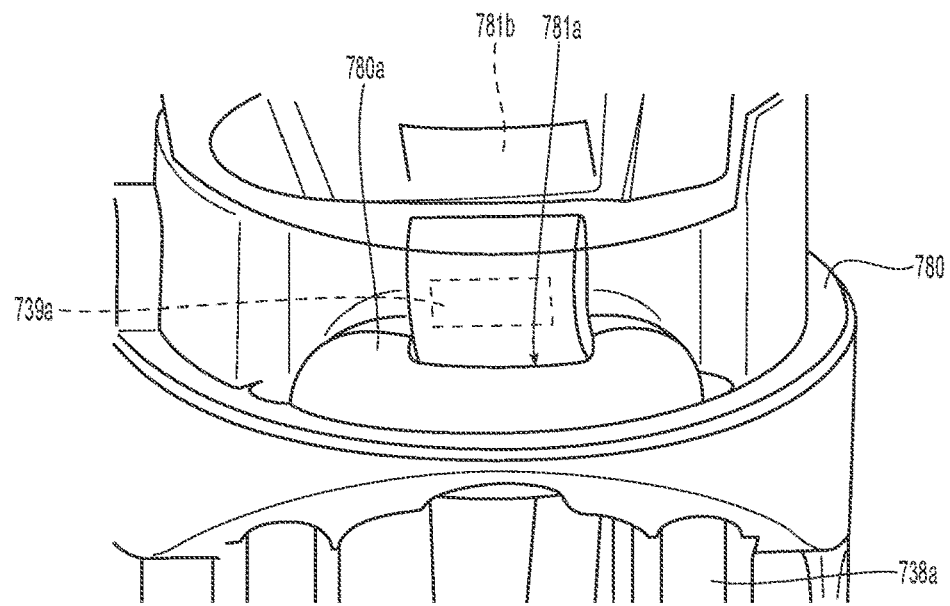

As mentioned above, distal link 780 couples to central link 710. More particularly, flanges 712a, 712b are configured to operably couple to corresponding mechanical interfaces 782a, 782b (See FIG. 5C) to allow selective articulation along plane "T" (FIG. 8A) upon translation of the articulation cables 738a, 738b. Articulation cables 738a, 738b are configured to extend from the articulation actuator 200, through the various components (e.g., end cap 770, seal 760, back transition plug 730, proximal link 720, central link 710, and distal link 780, and secure within predefined pockets 781a, 781b defined in the distal link 780 (FIG. 8C). Articulation cables 738a, 738b are configured as four distinct individual cables 738a1, 738a2, 738b1, 738b2 extending from the articulation actuator 200 that are grouped in opposing pairs (e.g., individual cables 738a1, 738a2 and 738b1, 738b2) and crimped together at crimps 739a, 739b, respectively, at their respective distal ends to form articulation cables 738a, 738b. Movement of one of the cables, e.g., individual cable 738a1, in the cable pair produces the opposite movement of the other cable, e.g., individual cable 738a2, of the cable pair. Crimping (or otherwise joining) the opposing articulation cables 738a, 738b simplifies manufacturing and assembly. Crimps 739a, 739b are configured to sit and anchor within respective pockets 781a, 781b (FIGS. 8B and 8C) defined in the distal link 780. The cables, e.g., individual cables 738a1, 738a2, are configured to extend through the various passageways, e.g., passageways 715 and 725, and are spaced as far as possible from one another to provide maximum torque for actuation purposes.

As mentioned above, proximal link 720 couples to central link 710. More particularly, flanges 711a, 711b are configured to operably couple to corresponding mechanical interfaces 721a, 721b (See FIGS. 9A and 9B) to allow selective articulation along plane "N" (FIG. 8A) upon translation of the articulation cables 738a, 738b. A pair of opposing flanges 722a, 722b extends from a distal end of the proximal link 720 on either side of passage 725. Articulation cables 738a, 738b extend through apertures 728a, 728b defined in a proximal end of the flanges 722a, 722b and ride a respective pair of opposing railways 723a, 723b defined in flanges 722a, 722b. Railways 723a, 723b extend around the distal end of the flanges 722a, 722b to guide each cable, e.g., cable 738a1 and 738a2, of each articulation cable, e.g., 738a, as the individual cables 738a1 and 738a2 move oppositely through the articulation assembly 700 upon actuation thereof. The articulation direction of the wrist 701, i.e., proximal link 720, central link 710 and distal link 780, is aligned with the jaw members 110, 120 for better visualization, e.g., side-to-side versus up and down.

Figure 9A:
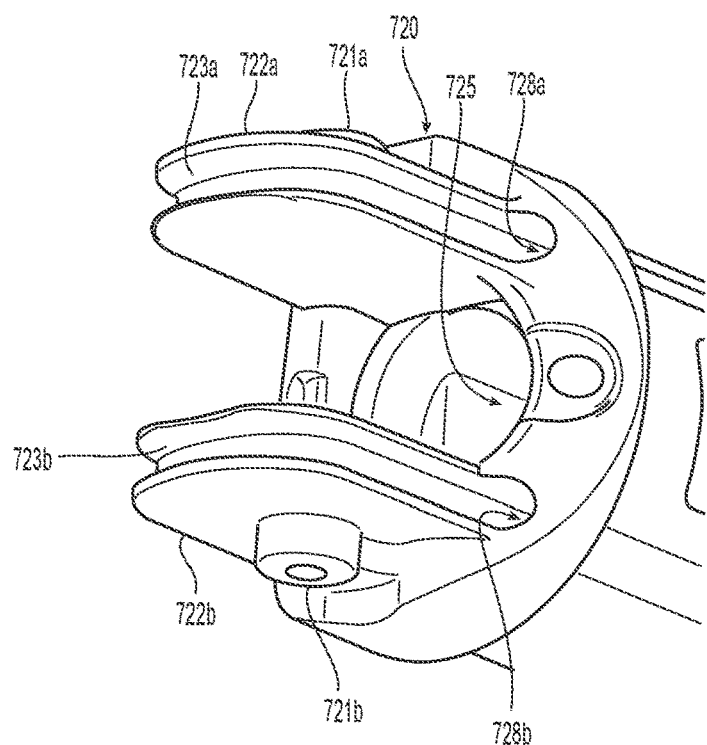
FIGS. 9A-9D are various views of a proximal link of the wrist assembly of FIG. 4A.
Figure 9B:
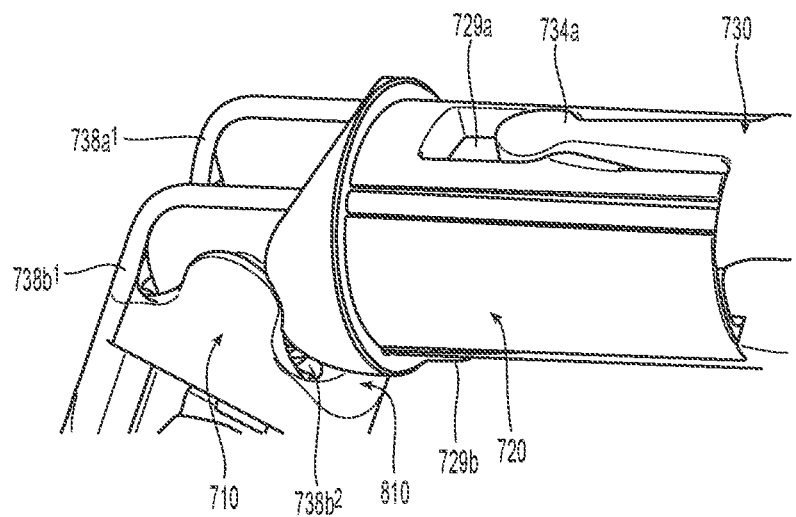
Figure 9C:
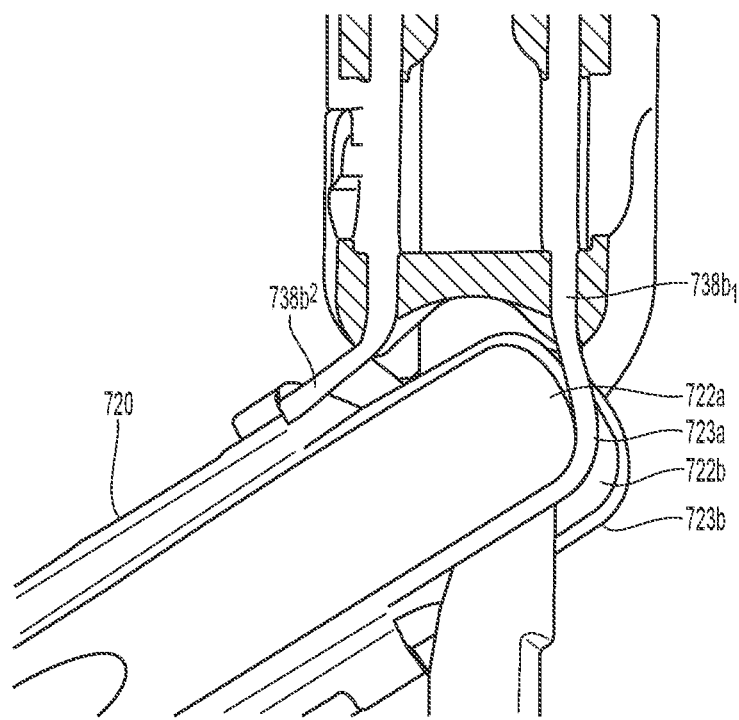
Figure 9D:
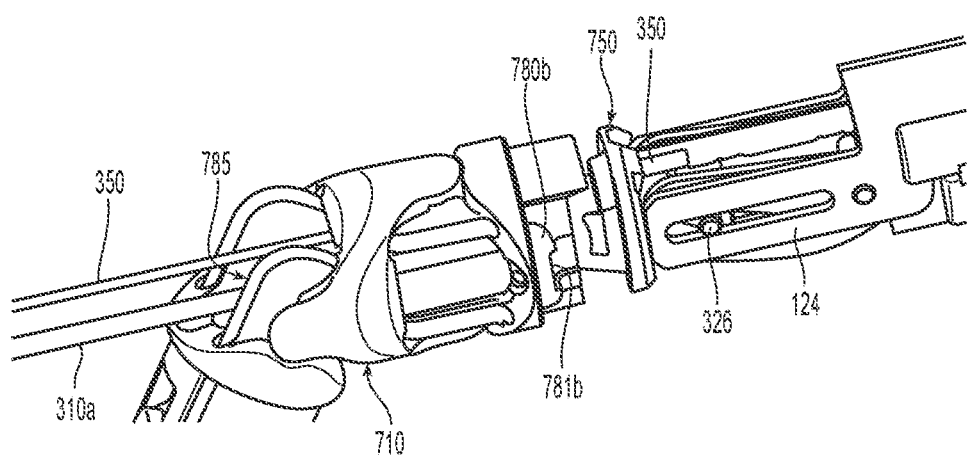

As mentioned above, during articulation, the cables, 738a1 and 738a2 move in opposite directions. The radius of each flange 722a, 722b is configured to compensate for the changes in length of the cables 738a1 and 738a2 during articulation so that the overall length of each cable 738a1 and 738a2 remains substantially constant. In other words, as the inner cable, e.g., cable 738a1, shortens during articulation, the outer cable, e.g., cable 738a2, increases in length along the respective flange 722a (FIG. 9C).

Back transition plug 730 operably couples to the proximal link 720 via a pair of opposing fingers 734a, 734b that are configured to mechanically engage a corresponding pair of opposing recesses 729a, 729b defined in the proximal link 720. Back transition plug 730 is configured to transition the various articulation cables 738a, 738b, leads 345a, 345b, cam rod 310a and blade rod 350 therethrough and into and through the wrist assembly 701 (e.g., links 720, 710 and 780) through various internal passageways defined therein, e.g., 731. One passageway, passageway 739, is configured to transition the cam or drive rod 310a and also configured to prevent buckling of the cam rod 310a therein. A long outer tube 310 may be disposed over the cam rod 310a to prevent buckling as well. Other passageways, e.g., passageways 736a, 736b, are configured to pass the blade rod 350 and leads 345a, 345b therethrough. Passageways 731 (FIG. 6F—shown in phantom) defined in the back transition plug 730 are configured to pass the articulation cables 738a, 738b, leads 345a, 345b therethrough.

A seal clip 770 operably couples to the back transition plug 730 via fingers 772a, 772b which are configured to mechanically engage corresponding apertures 732a, 732b defined within the back transition plug 730. Each finger and aperture interface, e.g., finger 772a and aperture 732a, may be configured at a different length than the other finger and aperture interface, e.g., finger 772b and aperture 732b, depending upon a particular purpose.

Figure 10A:
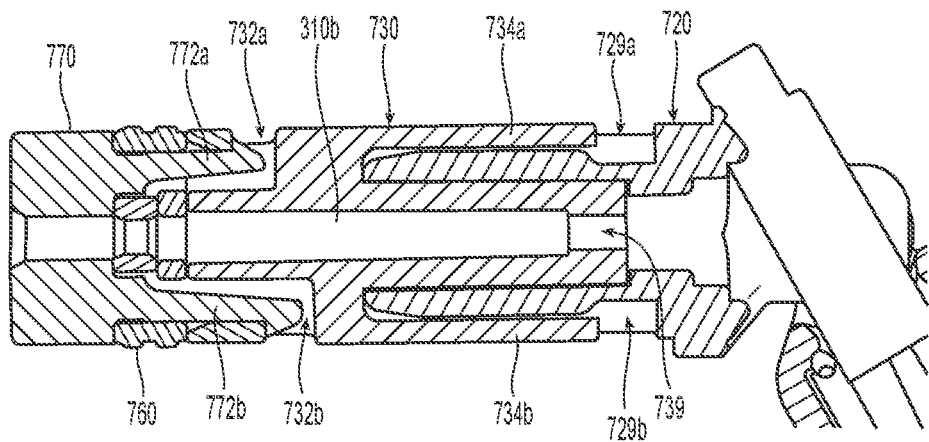
FIGS. 10A-10B are various views of a back transition plug of the wrist assembly of FIG. 4A.
Figure 10B:
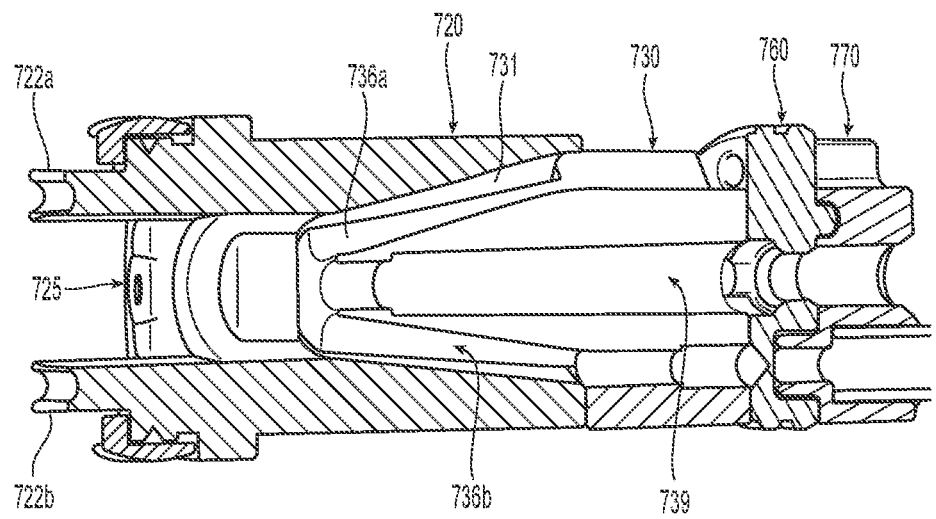

The seal clip secures a seal or O-ring 760 to the back transition plug 730 (FIGS. 10A and 10B). Seal ring 760 may be made from any type of material configured to seal the seal clip atop shaft 30 and to the back transition plug 730. Seal ring 760 is configured to seal around all the passthrough articulation cables 738, electrical leads 345a, 345b, etc. The seal ring 760 may be made from a material that seals the seal clip atop shaft 30 and to the back transition plug 730.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular configurations. Those skilled in the art will envision other modifications within the scope and spirit of the claims appended hereto.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended hereto.

What is claimed is:

1. An articulating electrosurgical instrument, comprising:
a housing having an elongated shaft extending therefrom;
a wrist assembly operably supported to a distal end of the elongated shaft and configured to support an end effector assembly at distal end thereof, the wrist assembly including:
a proximal link operably coupled to the distal end of the elongated shaft;
a distal link operably coupled to the end effector assembly; and
a central link operably coupled between the proximal link and the distal link;
a transition lumen configured to be received within at least the distal link, central link and proximal link, the transition lumen including a helical passageway defined therein configured to guide a blade rod therethrough for operable engagement with a blade disposed within the end effector assembly.

2. The articulating electrosurgical instrument according to claim 1, wherein the transition lumen includes a central passageway defined therein configured to guide a cam rod for reciprocation therethrough that actuates the end effector assembly upon translation thereof.

3. The articulating electrosurgical instrument according to claim 1, wherein the transition lumen includes a lead passageway defined therein configured to guide one or more electrical leads therethrough and into the end effector assembly.

4. The articulating electrosurgical instrument according to claim 1, wherein a proximal end of the transition lumen is keyed to mechanically engage a corresponding mechanical interface disposed within the proximal link.

5. The articulating electrosurgical instrument according to claim 1, wherein a distal end of the transition lumen includes a cap configured to mechanically engage a corresponding mechanical interface disposed at a distal end of the distal link.

6. The articulating electrosurgical instrument according to claim 1, wherein the transition lumen includes a cap configured to mechanically engage a corresponding mechanical interface disposed at a distal end of the distal link, a key-like interface disposed at a proximal end thereof configured to mechanically engage a corresponding mechanical interface disposed within the proximal link, and a stem disposed therebetween.

7. The articulating electrosurgical instrument according to claim 6, wherein the transition lumen includes a taper disposed between the cap and the stem configured to facilitate engagement within distal link.

8. The articulating electrosurgical instrument according to claim 6, wherein the cap is configured to receive a transition plug therein, the transition plug operably coupling to the end effector assembly.

9. The articulating electrosurgical instrument according to claim 8, wherein the transition plug includes opposing tangs on an outer surface thereof configured to receive complementary mechanical interfaces defined within the transition lumen to secure the transition plug within the transition lumen.

10. The articulating electrosurgical instrument according to claim 8, wherein the transition plug includes a passageway defined therein configured to guide the blade rod therethrough for operable engagement with the blade disposed within the end effector assembly.

11. The articulating electrosurgical instrument according to claim 8, wherein the transition plug includes a central passageway defined therein configured to guide a cam rod for reciprocation therethrough that actuates the end effector assembly upon translation thereof.

12. The articulating electrosurgical instrument according to claim 8, wherein the transition plug includes a lead passageway defined therein configured to guide one or more electrical leads therethrough and into the end effector assembly.

13. The articulating electrosurgical instrument according to claim 10, wherein the passageway of the transition plug and the helical passageway of the transition lumen are disposed in registration with one another to facilitate guiding the blade rod into the end effector assembly.

14. The articulating electrosurgical instrument according to claim 8, wherein a central passageway defined in the transition plug and a central passageway defined in the transition lumen are disposed in registration with one another to facilitate reciprocation of a cam rod therethrough that actuates the end effector assembly upon translation thereof.

15. The articulating electrosurgical instrument according to claim 8, wherein a cut-out defined in the transition plug and a lead passageway defined in the transition lumen are disposed in registration with one another to facilitate reception of one or more electrical leads therethrough.

16. The articulating electrosurgical instrument according to claim 8, wherein the transition lumen is made from a rubber-like or compliant material configured to bend upon articulation of the wrist assembly.

17. The articulating electrosurgical instrument according to claim 16, wherein the transition lumen is made from a moldable thermoplastic polyurethane.

* * * * *